US009352316B2

(12) United States Patent
Robertson et al.

(10) Patent No.: US 9,352,316 B2
(45) Date of Patent: May 31, 2016

(54) CAPILLARY FLUID FLOW CONTROL

(71) Applicant: CARCLO TECHNICAL PLASTICS LIMITED, Ossett, Yorkshire (GB)

(72) Inventors: Philip Robertson, Weybridge (GB); Richard Swainson, Chessington (GB); Patrick Ward, Croydon (GB)

(73) Assignee: CARCLO TECHNICAL PLASTICS LIMITED, Ossett, Yorkshire (GB)

( * ) Notice: Subject to any disclaimer, the term of this patent is extended or adjusted under 35 U.S.C. 154(b) by 0 days.

(21) Appl. No.: 14/697,721

(22) Filed: Apr. 28, 2015

(65) Prior Publication Data

US 2015/0238957 A1 Aug. 27, 2015

Related U.S. Application Data

(62) Division of application No. 14/004,750, filed as application No. PCT/GB2012/050573 on Mar. 15, 2012, now Pat. No. 9,044,757.

(30) Foreign Application Priority Data

Mar. 15, 2011 (GB) .................................. 1104354.4
Mar. 15, 2011 (GB) .................................. 1104357.7
Mar. 15, 2011 (GB) .................................. 1104358.5
Mar. 15, 2011 (GB) .................................. 1104359.3

(51) Int. Cl.
*G01N 15/06* (2006.01)
*G01N 33/00* (2006.01)
(Continued)

(52) U.S. Cl.
CPC ........... *B01L 3/50273* (2013.01); *B01L 3/5027* (2013.01); *B01L 3/502707* (2013.01); *B01L 3/502738* (2013.01); *B01L 3/56* (2013.01); *B01L 3/561* (2013.01); *B01L 2200/0689* (2013.01);
(Continued)

(58) Field of Classification Search
CPC ........ G01N 15/06; G01N 33/00; G01N 33/48
USPC .................... 422/68.1, 81, 82, 502, 503, 504; 436/43, 174, 180
See application file for complete search history.

(56) References Cited

U.S. PATENT DOCUMENTS 3,620,676 A * 11/1971 Davis ............................ 422/405
3,994,594 A * 11/1976 Sandrock et al. ............. 356/246
(Continued)

FOREIGN PATENT DOCUMENTS

CN 1067113 A 12/1992
EP 0 504 738 A1 9/1992
(Continued)

OTHER PUBLICATIONS

United Kingdom Search Report dated Jul. 15, 2011, issued in connection with Application No. GB 1104358.5.
(Continued)

*Primary Examiner* — Brian J Sines
(74) *Attorney, Agent, or Firm* — Nixon & Vanderhye P.C.

(57) ABSTRACT

A fluid flow control device controls flow of fluid in a capillary pathway device having a first capillary passage with an inlet and an outlet and a fluid application region for receiving a liquid sample for entry to the capillary passage via the inlet, with the fluid flow control device comprising first sealing means operable for releasably sealing the outlet of the first capillary passage.

19 Claims, 14 Drawing Sheets

(51) Int. Cl.
*G01N 33/48* (2006.01)
*B01L 3/00* (2006.01)

(52) U.S. Cl.
CPC ........ *B01L 2200/16* (2013.01); *B01L 2300/042* (2013.01); *B01L 2300/0672* (2013.01); *B01L 2300/161* (2013.01); *B01L 2400/0406* (2013.01); *B01L 2400/049* (2013.01); *B01L 2400/0683* (2013.01); *B01L 2400/0694* (2013.01); *B01L 2400/082* (2013.01); *Y10T 436/2575* (2015.01)

(56) References Cited

U.S. PATENT DOCUMENTS

| | | | | |
|---|---|---|---|---|
| 4,088,448 | A | | 5/1978 | Lilja et al. |
| 4,233,029 | A | | 11/1980 | Columbus |
| 4,426,451 | A | * | 1/1984 | Columbus ..................... 436/518 |
| 4,761,381 | A | * | 8/1988 | Blatt et al. ..................... 436/165 |
| 4,902,629 | A | * | 2/1990 | Meserol et al. ............... 436/165 |
| 4,963,498 | A | | 10/1990 | Hillman et al. |
| 5,047,206 | A | * | 9/1991 | Dombrowski ................ 422/412 |
| 5,144,139 | A | * | 9/1992 | Hillman et al. ............ 250/341.3 |
| 5,164,598 | A | | 11/1992 | Hillman et al. |
| 5,200,152 | A | * | 4/1993 | Brown .......................... 422/503 |
| 5,228,350 | A | | 7/1993 | Karpf et al. |
| 5,278,079 | A | | 1/1994 | Gubinski et al. |
| 6,017,494 | A | | 1/2000 | Ashihara et al. |
| 6,561,208 | B1 | | 5/2003 | O'Connor et al. |
| 2001/0046453 | A1 | | 11/2001 | Weigl et al. |
| 2004/0184964 | A1 | | 9/2004 | Watanabe |
| 2006/0183216 | A1 | | 8/2006 | Handique et al. |
| 2008/0006530 | A1 | | 1/2008 | Winarta et al. |
| 2011/0002812 | A1 | | 1/2011 | Asogawa |
| 2011/0003286 | A1 | | 1/2011 | Hanafusa et al. |
| 2014/0004019 | A1 | | 1/2014 | Robertson et al. |
| 2014/0079603 | A1 | | 3/2014 | Kanai |

FOREIGN PATENT DOCUMENTS

| | | | |
|---|---|---|---|
| EP | 1500937 | | 1/2005 |
| EP | 2282190 | | 2/2011 |
| GB | 1140149 | | 1/1969 |
| JP | 2004-170408 | | 6/2004 |
| JP | 2004-286501 | | 10/2004 |
| JP | 2005-512071 | | 4/2005 |
| JP | 2006-520898 | | 9/2006 |
| JP | 2007-101240 | | 4/2007 |
| JP | 2007-139658 | | 6/2007 |
| JP | 2009-506332 | | 2/2009 |
| JP | 2009-63597 | | 3/2009 |
| WO | WO03/049860 | | 6/2003 |
| WO | WO 03/049860 | A1 | 6/2003 |
| WO | WO 03/076937 | A3 | 9/2003 |
| WO | WO2004/083859 | | 9/2004 |
| WO | WO 2006/116616 | A3 | 11/2006 |
| WO | WO2007/025559 | | 3/2007 |
| WO | WO 2007/148285 | | 12/2007 |
| WO | WO 2007/148285 | A2 | 12/2007 |
| WO | WO 2008/006503 | A1 | 1/2008 |
| WO | WO 2008/119470 | A1 | 10/2008 |
| WO | WO 2009/035062 | | 3/2009 |
| WO | WO 2009/063681 | A1 | 5/2009 |
| WO | WO 2009/078107 | | 6/2009 |
| WO | WO2009/145172 | | 12/2009 |
| WO | WO 2010/056185 | A1 | 5/2010 |
| WO | WO 2010/138077 | A1 | 12/2010 |

OTHER PUBLICATIONS

United Kingdom Search Report dated Jul. 15, 2011, issued in connection with Application No. GB 1104359.3.
International Search Report for PCT/GB2012/050573 mailed Jun. 20, 2012.
Written Opinion of the International Searching Authority mailed Jun. 20, 2012.

* cited by examiner

CAPILLARY FLUID FLOW CONTROL

This application is a divisional of application Ser. No. 14/004,750 (published as US 2014-0004019 A1), filed Sep. 12, 2013 (issued as U.S. Pat. No. 9,044,757), which is a U.S. national phase of International Application No. PCT/GB2012/050573 filed 15 Mar. 2012 which designated the U.S. and claims priority to GB 1104354.4 filed 15 Mar. 2011, GB 1104357.7 filed 15 Mar. 2011, GB 1104358.5 filed 15 Mar. 2011, and GB 1104359.3 filed 15 Mar. 2011, the entire contents of each of which are hereby incorporated by reference.

FIELD OF THE INVENTION

This invention relates to a fluid flow control device for controlling flow of fluid in a capillary pathway device, and a capillary pathway device, such as a sample testing device, incorporating such a fluid flow control device.

BACKGROUND TO THE INVENTION

There are many situations in which control of fluid flow is required. For example, it is often desirable to provide a predetermined quantity of a liquid sample e.g. for testing purposes, and difficulties can arise in achieving this accurately and reliably in an easy manner not requiring complex equipment and/or skilled operators, particularly where very small quantities of liquid are involved. This applies e.g. with sample testing devices having one or more capillary passages for testing for the presence or amount of a component of interest in a liquid sample, commonly a body fluid such as blood (whole blood or plasma), urine, saliva, etc.

In the prior art, flow of liquid sample though a device is typically controlled by a system using external motive force, for example syringes and bellows (see for example US2001/0003286). Such equipment requires the device to be complex, and as a result, more expensive and not suited to the Point of Care market.

The present inventions to overcome or ameliorate some or all of the problems associated with the prior art.

SUMMARY OF THE INVENTION

In one aspect, the present invention provides a fluid flow control device for controlling flow of fluid in a capillary pathway device having a first capillary passage with an inlet and an outlet and a fluid application region for receiving a liquid sample for entry to the capillary passage via the inlet, the fluid flow control device comprising first sealing means operable for releasably sealing the outlet of the first capillary passage.

The present invention is typically applicable to capillary pathway devices in which fluid flow is passive, i.e. it is not controlled by an external force. The first sealing means of the fluid flow control device act as a remote (off-line) valve, which control passive flow of sample liquid through a passage of the capillary pathway device. Thus, the sealing means are releasably movable between a position in which the sealing means are positioned to seal an outlet and a position in which the outlet is not sealed, to stop or allow liquid sample flow, respectively. By remote or off-line is meant that the valve (sealing means) is capable of controlling flow of a liquid sample (i.e. stopping or slowing, or resuming flow) without requiring contact between the sealing means and liquid sample. When a liquid sample is applied to the fluid application region, liquid will flow along the first capillary passage only when the first sealing means is operated not to seal the outlet of the capillary passage. When the first sealing means is operated to seal the outlet, then fluid flow along the capillary passage is not possible. Thus operation of the first sealing means can be used to control fluid flow in the first capillary passage.

The present invention provides a fluid flow control device, as described herein, in combination with a capillary pathway device, as described herein.

In an aspect of the invention there is provided a device comprising a fluid flow control device for controlling flow of fluid in a capillary pathway device, in combination with a capillary pathway device comprising a first capillary passage with an inlet and an outlet and a fluid application region for receiving a liquid sample for entry to the capillary passage via the inlet, the fluid flow control device comprising first sealing means operable for releasably sealing the outlet of the first capillary passage. Preferably, the fluid flow control device and capillary pathway device are integrated to form a single device. Alternatively, the fluid flow control device (or part thereof) may be releasable from the capillary pathway device. In such an embodiment, the fluid flow control device may be arranged to cooperate with the capillary pathway device.

The capillary pathway device may comprise a single capillary passage, but may have two or more capillary passages. For instance the capillary pathway device may have a second or further (third, fourth, fifth etc) capillary passage, each with an inlet and an outlet, and the fluid flow control device may comprise a second or further (third, fourth, fifth etc) first sealing means operable for releasably sealing a respective outlet of a second or further capillary passage. Thus, in a device comprising a second or further capillary passage, flow of liquid sample in each passage is controlled by (preferably separate) first sealing means provided in respect of each passage.

In one arrangement, the capillary pathway device comprises first and second (and possibly more) similar capillary passages, typically in a side-by-side arrangement. The passages may have a common inlet and respective outlets. By appropriate operation of the first sealing means, liquid applied at the fluid application region may be caused to flow along each of the capillary passages as required, for desired time intervals (and hence in desired quantities). In this way, the fluid flow control device may be used, for instance, to dispense liquid from a common source to different outlets in desired quantities at desired times.

The invention is used by applying a sample to the fluid application region, with the first sealing means operated to not seal the capillary passage. Liquid sample will flow from the fluid application region into a first or second or further capillary passage. Flow of liquid sample can be slowed or stopped at any point during the assay, by operating the first sealing means to partially or fully close the outlet(s) of the capillary passage. Preferably, the first sealing means may then be operated to not seal the outlet(s) of the capillary passage, allowing liquid sample to flow along the capillary passage. Flow of the liquid sample may be slowed, stopped and caused to resume flow by appropriate movement of the first sealing means, any number of times (one or more) during a single assay.

The present invention also has the advantage of providing a simple mechanism by which flow of liquid sample can be slowed or stopped. This may be desirable in a multi-step assay, for example at a predetermined point to enable a reaction to occur before allowing the fluid to proceed to the next step. The invention can also be used to direct fluid, or a portion of fluid, along different capillary passages in a device.

In this aspect of the invention, substantially all liquid sample will flow from the fluid application region into a capillary passage. Typically, for a sampling based assay, a defined volume of liquid sample may be required for optimal functioning of the assay. Thus, in a preferred embodiment, sample metering means may be provided, which service to provide a predetermined, measured volume of liquid to a capillary passage for the assay. Any suitable sample metering means may be used, which may vary depending upon the form and purpose of the assay and device.

In an aspect of the invention, there is provided a device comprising a fluid flow control device for controlling flow of fluid in a capillary pathway device, in combination with a capillary pathway device comprising a first capillary passage with an inlet and an outlet and a fluid application region for receiving a liquid sample for entry to the capillary passage via the inlet, the fluid flow control device comprising first sealing means operable for releasably sealing the outlet of the first capillary passage, wherein the device is further in combination with sample metering means for metering a predetermined volume of sample liquid to a portion of a capillary passage. Preferably, the fluid flow control device, capillary pathway device and metering means are integrated to form a single device. Preferably, sample metering means may be provided either in the fluid flow control device or the capillary pathway device.

In a preferred arrangement for sample metering, the capillary pathway device comprises a first capillary passage (or second or further capillary passage, as defined above) and a side passage, extending from the first capillary passage part way along the length thereof and leading to an outlet, the inlet to the side passage being constituted by the junction with the first capillary passage. The fluid flow control device comprises first sealing means operable for releasably sealing the outlet of a first capillary passage and second sealing means operable for releasably sealing the outlet of the side passage.

In such an embodiment, the invention is used by applying a liquid sample to the fluid application region, with the first sealing means operated to seal the capillary passage outlet and the second sealing means operated not to seal the outlet of the side passage. Liquid sample flows along the capillary passage by capillary action only as far as the intersection with the side passage, because the outlet of capillary passage is sealed. Liquid is, however, able to flow into and along the side passage because the side passage outlet is not sealed. The main capillary will fill until all sample has been drawn in, and the well is depleted of sample liquid. Any excess liquid above the test volume will begin to fill the side passage. Flow stops when all sample has drawn in from the fluid application region into the capillary passage (the back pull in the capillary then equaling the forward pull). In this way, the capillary passage is filled with sample liquid to a defined point (the intersection with the side passage). The volume of sample liquid from the capillary passage inlet to the intersection with the side passage is referred to herein as a test volume. Any excess sample over the test volume is contained within the side channel. If the sample volume is too small, liquid sample will not reach the side passage. Thus, it is preferred that sample in excess of the test volume is added to the device. Preferably, the test volume is a pre-determined volume, appropriate to the assay type. The conditions of the sealing means are then reversed, with the first sealing means functioning not to seal the capillary passage outlet and the second sealing means functioning to seal the side passage outlet. The liquid in the capillary passage is then free to flow further along the capillary passage, for example by capillary action. No further flow will take place along the side passage, including back-flow towards the capillary passage. Where the liquid sample moves by capillary action it is usually desirable to add a chase buffer to the proximal part of the capillary, e.g. via the sample port. Where other motive forces are used to cause the liquid sample to flow, the addition of a chase buffer may not be necessary.

The above embodiment has the advantage that the leading edge of the sample liquid is not used as the test fluid, but is removed into a side passage as excess fluid. This is different to the assays of the prior art, where the leading volume is used as the test volume. This has benefit in applications where mid-sample liquid is preferred, for example urine for pregnancy test. Further, the arrangement means that the defined sample does not leave the main capillary, and so can continue to flow along the capillary channel for the assay. No complex fluidics or additional sources of motive force are required other than capillary force. Further, the design is such that excess sample is contained safely within the device preventing any external contamination.

The invention can thus provide a simple, convenient and reliable means for controlling the flow of small volumes of liquid, preferably also for obtaining a predetermined volume of a liquid sample in a capillary passage (the test volume). As mentioned above, a test volume may be metered using any suitable means. Where a side passage is provided for sample metering, the size of the test volume depends on the cross-sectional area and length of the capillary passage between the inlet and the side passage inlet. The size of the capillary passage between the inlet and side passage inlet (the test volume) may be of any suitable size, depending upon the purpose of the assay. Preferred test volumes (and thus volume of the capillary passage between the inlet and the intersection with the side passage) range from 1 to 200 μl, more preferably between 1 and 150 μl, more preferably between 1 and 50 μl, more preferably between 1 and 20 μl, more preferably between 1 and 10 μl.

Thus, the sealing means act, in the present invention, as remote valves, operation of which serves to control flow in the capillary and where provided, the side passages. The sealing means are provided externally to the passages, and therefore are capable of controlling flow of a liquid sample in the capillary passage without contact of the sealing means with the liquid sample. Thus, the sealing means are effectively off-line valves for control of liquid sample flow, such that they are capable of controlling flow of a liquid sample in a capillary passage without requiring contact between the sealing means and liquid sample (i.e. they operate at a distance from the leading edge of the fluid).

Sealing means for use in the present invention must be sufficient to provide an air tight seal to a passage, when in a sealing relationship with an outlet. An air tight seal will substantially or completely stop fluid flow in the capillary passage to which the sealed outlet is related.

The fluid flow control device is preferably applicable to any capillary pathway device, and finds application in a variety of microfluidic applications that require delivery or control of one or more liquids. Thus, it may be applicable to a microfluidic device, including for example inkjet printheads, DNA chips, lab-on-a-chip technology, biotechnology based arrays, and microfluidic based sample assays, micro-propulsion, and micro-thermal technologies. The fluid flow control device may be provided in combination with devices which rely on other motive forces than capillary action to drive fluid flow, preferably as an integrated device. In such embodiments, reference to capillary action and capillary passages herein include within their scope any applicable fluid flow action or passage.

The invention is preferably used for sampling based assays, where a measured volume of liquid is removed from a larger volume and assayed. The present invention is particularly suited for use in assaying a sample liquid for a particular component. Whilst it may be suited to biological and non-biological applications, it is particularly suited to the former. Thus, the present invention is preferably for use in assaying a biological sample for a particular component, for example an analyte. Typically, assays for which the present invention may be used are microfluidics-based assays, including for example agglutination based assays, capture-based assays such as ELISA assays, and coagulation based assays. The assays may be quantitative or qualitative. The present invention may be suitable for use with any liquid sample. Preferred biological samples for assay using the present invention are blood (whole blood or plasma) and urine.

The invention finds particular application in sample testing devices having one or more capillary passages for testing for the presence of a component of interest in a liquid sample, e.g. blood or other body fluid, as is well known in the art, e.g. diagnostic assays, such as the agglutination assays disclosed in WO 2004/083859 and WO 2006/046054. Thus, in an aspect there is provided a sample testing device comprising a fluid flow control device for controlling flow of fluid in a capillary pathway device, in combination with a capillary pathway device comprising a first capillary passage with an inlet and an outlet and a fluid application region for receiving a liquid sample for entry to the capillary passage via the inlet, the fluid flow control device comprising first sealing means operable for releasably sealing the outlet of the first capillary passage. Preferably, the fluid flow control device and capillary pathway device are integrated to form a single sample testing device. Alternatively, the fluid flow control device (or part thereof) may be releasable from the capillary pathway device. In such an embodiment, the fluid flow control device may be arranged to cooperate with the capillary pathway device. Preferably, the sampling testing device comprises sample metering means, as described herein.

The capillary pathway device of the sample testing device as defined herein may include at least two capillary channels, preferably with associated features as described herein, constituting a test (or assay) track and a control track. Typically, these will have a common inlet and respective, separate, outlets. Preferably metering means will be provided in the sample testing device to control sample volume for each capillary passage, for example a side passage associated with each capillary passage, as defined herein. Multiple test tracks may be provided, for simultaneous testing for multiple components of interest.

A device of the present invention may comprise reagent deposited in one or more capillary passages. Typically, side passages which are provided for removal storage of excess sample do not require reagent deposited therein. Any suitable methods may be used for deposition of reagent in a capillary channel. Reagents laid down in a capillary channel may include, for example, agglutination reagents, antibodies, and labels. Other reagents include buffers, and any other assay components.

In a sample testing device, the capillary passage typically incorporates a reagent system capable of causing a reaction with a component of interest. Preferably, reagent may be deposited in test (assay) and/or control passages (i.e. main capillary passages). In the case of the arrangement described above, the reagent system is typically deposited in a capillary passage. Where a side passage is provided for metering, any test reagent is preferably deposited downstream thereof. Other sample treatment reagents (for example, an anticoagulant) may be provided upstream of the junction with a side passage.

The two arrangements discussed above may be used together. Thus, for example, the capillary pathway device may include two or more sets of a main (first) capillary passage with an associated side passage. First sealing means are provided to releasably operate the outlet of a main passage. Second sealing means are provided to releasably seal the outlet of a side capillary passage.

In the present invention, a capillary passage may have any suitable geometry, typically dictated by the array type. For instance, the passage may be straight, curved, serpentine, U-shaped, etc. The cross-sectional configuration of the capillary passage may be selected from a range of possible forms, e.g. triangular, trapezoidal, square, rectangular, circular, oval, U-shaped, etc. The capillary passage may have any suitable dimensions. Typical dimensions of a capillary passage for use in the invention is a depth of 0.1 mm to 1 mm, more preferably 0.2 mm-0.7 mm. The width of a channel may be of similar dimensions to the depth. Where the channel is V-shaped, for example, the profile may be that of an equilateral triangle, each side having a length of between 0.1 and 1 mm, more preferably between 0.2 and 0.7 mm.

Where more than one capillary passage is provided in a device, the geometry of each may be independently selected and two or more may be the same or different.

A side passage may also be a capillary passage, or may be a larger passage or storage channel. The size and shape of a side passage is typically dictated by the volume of sample it is required to accommodate. As the side passage is provided for storage of surplus sample, the same requirements of a test capillary passage, e.g. in terms of flow, reagent depositions, surface preparation, may not necessarily apply. The geometric and cross-sectional configurations of a side passage may be dictated by required volume to be held and the overall configuration of the device. Thus, it may be in the form of a passage, or another shape. The side passage may be wider or able to accommodate a larger volume than the test volume. For reasons including flow of sample, the side passage may be wider than the capillary passage. Preferably, the side passage has a volume of between 1 and 100 μl.

Typical dimensions of a side passage for use in the invention is a depth of 0.1 mm to 1 mm, more preferably 0.2 mm-0.5 mm, most preferably approximately 0.4 mm. The width of a channel may be of similar dimensions to the depth. Typically, a side passage will have any length suitable depending upon the estimated sample size and the metering requirement, and also dictated by the shape and form of the device as a whole. Preferably, the side passage may have a length of between 20 and 100 mm, more preferably between 20 and 80 mm, more preferably approximately 60 mm.

A side passage may branch from the capillary passage in any direction, and may adopt any geometric configuration, for example it may be straight, curved, serpentine, U-shaped etc. For all or part of its length, it may extend parallel to the capillary passage, or perpendicular thereto. Preferably, the side passage is configured such that the side passage outlet is in close proximity to the capillary passage outlet, for ease of operation. The cross-sectional configuration may be any suitable configuration, for example trapezoidal, triangular, horizontal, square, rectangular, circular, over, or U-shaped etc.

Functionally, the configuration of the side passage is preferably such that it can be remotely (i.e. at a distance from the leading edge of the fluid) controlled by sealing or opening the side passage outlet.

In a preferred embodiment, a capillary passage may comprise means for detecting presence or absence of sample liquid. Such means may be used to communicate to the user that further operation of the device (e.g. sealing or not sealing an outlet) is necessary, and/or to monitor flow for the purpose of obtaining assay results. A side passage may comprise means for detecting the presence or absence of sample liquid, preferably to confirm that sample liquid has entered the side passage, and therefore the test volume is present in the main capillary passage (i.e. the volume is not short or insufficient). Suitable detection means for use in the invention may include, in a simple form, for example a viewing window, or other means such as an electronic or optical sensor. A detections means may be operably linked to a control element, for operation of a sealing means of the device.

Inlets typically mean entry holes which are in fluid communication with the sample application region, preferably in direct fluid communication. If in indirect communication, this is preferably via non-capillary passages or means. An inlet is preferably provided at a proximal end of a capillary or side passage of the invention, although inlets may also be provided at one or more positions along the length of a capillary or side passage, for example for deposition of reagents in a passage or where branched (converging) channels or passages are provided. An inlet must be of a dimension which enables it to receive liquid. Preferably, for a sample testing device, an inlet will have an opening diameter in the region of 2 and 4 mm, preferably between 1 and 2 mm. For other applications, larger or smaller inlets are envisaged.

Typically, an outlet of a capillary passage or side passage are provided to enable flow through a passage, for example by capillary of by a motive force, typically so that air can leave the passage. An outlet may be provided at a distal end of a capillary or passage, although an outlet may be provided at one or more positions along the length of a capillary or side passage. An outlet may not need to accommodate liquid flow therethrough. Preferably, it is able to accommodate air flow therethrough, sufficient to maintain flow of a liquid through the respective passage. For a sample testing device, an outlet may be of smaller dimensions than an inlet. An outlet may typically have an opening diameter of between 0.5 mm and 4 mm, more preferably between 0.75 and 2 mm. For other devices, larger or smaller outlets are possible. An outlet is typically only in fluid communication with a passage.

Outlets and inlets may have a raised skirt around circumference, with the outlet being central thereto.

A capillary testing device conveniently comprises a moulded plastics component, e.g. in the form of a generally planar element having grooves in one surface thereof to define the capillary passage(s) when sealed by a cover member.

In an embodiment, a device of the invention comprises fluid dispensing means, comprising a rupturable, sealed container of fluid to be dispensed, rupturing means for rupturing the container and releasing the contents, the container and/or rupturing means being arranged for relative movement between a first position in which the container is intact and a second position in which the container is ruptured.

The device preferably comprises a well, in fluid communication with the fluid application region, which may comprise a sample application hole leading to a capillary passage. The well may be any suitable shape and size, suitable for receiving and retaining liquid sample. The well may be provided (in full or in part) by the capillary pathway device, by the fluid flow control device or by fluid dispensing means. Preferably, the well may be formed within a planar element forming the capillary pathway device, for example as a concave region leading to a sample application hole. Alternatively, it may be defined by an upstanding portion of the capillary pathway device, such as a collar. In these embodiments, the base of the well may comprise fluid application region of the device. Alternatively, the well may be provided as part of the fluid flow control device. Alternatively, the well may be defined by a separate element, operably linked to the fluid application region by fluid communication means. In such an embodiment, the base of the well does not comprise fluid application region. In embodiments, the well may be formed by a combination of one or more elements forming the fluid flow control device, capillary pathway device and a separate element. For example, a base of the well may be formed by a portion of a capillary pathway device, and side walls of a well may be formed by a portion of a fluid flow control device, with a further, optionally separable, element provided to form a cap or cover for the well.

The well is conveniently constituted by one or more side walls, e.g. of generally circular cylindrical form. Preferably the base of the well is funnel shaped, i.e. configured such that it slopes toward a sample inlet hole from all directions. This configuration aids drainage of sample into a capillary passage. Preferably the well comprises a suitable form of cap or cover, which is preferably removable, and may constitute one or more side walls of the well.

The cap of a sample well may be fixed (i.e. not releasable) or may be releasable therefrom. A cap of a sample well may comprise a liquid inlet for passage of liquid to the fluid application region, and thus the sample application hole.

A well may comprise features, for example micropillars, to aid sample liquid flow into a capillary passage. Suitable features will be known to a person skilled in the art.

The fluid application region is designed to receive a larger volume of liquid sample than a test volume (for the or all associated capillary passages) to ensure filling of the capillary passage(s) up to the location of any side passages(s) (i.e. the test volume) and flow of excess liquid into the side passage(s).

The sealing means (and additional sealing means if present) may be located on a control element, movable to cause operation of the sealing means.

The control element is typically arranged for rotary movement or linear movement (axially, towards and away from the outlet, or laterally, in a sliding action).

In embodiments having more than one capillary passage, each with associated sealing means, two or more sealing means (and additional sealing means if present) may be constituted by a single sealing component provided by the fluid flow control device. A sealing component may be movable between a first position in which a sealing means of the sealing component seals an outlet, and a second or further sealing means of a sealing component does not seal an outlet; and a second position in which a first sealing means of a sealing component does not seal an outlet and a second or further sealing means of a sealing component seals an outlet. Alternatively, the sealing component is movable between a first position where two or more sealing means of the sealing component seal the outlets of the capillary passages; and a second position in which two or more sealing means of the sealing component do not seal the outlet of the capillary passages. Preferably, such a sealing component is conveniently located on a control element, e.g. arranged for rotary or linear (lateral) motion, movable to bring the sealing component into and out of a sealing relationship with each of the outlets.

Alternatively, one or more (and possibly further) sealing means may be provided for each of the capillary passage outlets, each operable for sealing the associated outlet or not. For instance, each sealing means may be located on a respective control element, e.g. arranged for linear or rotary movement towards and away from the associated outlet. As a further possibility, one or more sealing components may be located on a common control element, e.g. arranged for rotary or linear (lateral) motion, towards and away from one or more outlets.

In embodiments where a main capillary passage is associated with a side passage, first and second sealing means may be provided. In embodiments having two or more capillary passages, one or more of said capillary passages having a side passage, one or more pairs of first and second sealing means may be provided. One or more pairs of sealing means may be constituted by a single sealing component or provided on a control element. A sealing component may be provided on a control element. Such a component or control element is moveable between a first position in which the first sealing means is positioned to seal the outlet of the first capillary passage and the second sealing means is positioned not to seal the outlet of the side passage and a second position in which the first sealing means is positioned not to seal the outlet of a capillary passage and the second sealing means is positioned to seal the outlet of the side passage. In an embodiment, two or more first sealing means may be constituted by a single sealing component or provided on a control element. A sealing component may be provided on a control element. Such a component or control element may be moveable between a first position in which the first sealing means is positioned to seal the outlet of the first capillary passage and a second position in which the sealing means are positioned not to seal the outlet of a first capillary passage. Two or more second sealing means may be constituted by a single sealing component or provided on a control element. A sealing component may be provided on a control element. Such a component or control element may be moveable between a first position in which the sealing means are positioned to not seal an outlet of a side passage and a second position in which the sealing means are positioned to seal an outlet of a side passage. In an embodiment, two or more first sealing means and two or more second sealing means, or two or more components may be provided on the same control element, which is moveable between a first position in which the first sealing means is positioned to seal the outlet of the first capillary passage and the second sealing means is positioned to not seal the outlet of the side passage; and a second position in which the first sealing means are positioned not to seal the outlet of a first capillary passage and the second sealing means are positioned to seal the outlet of a side passage.

In an embodiment, sealing means may operate in a binary manner between two positions, a position in which an outlet is sealed and a position in which an outlet is not sealed. In another embodiment, a sealing means may operate in a quantitative manner such that the sealing means may be operated to partially close an outlet, such that the rate of flow of the liquid sample in a passage may be controlled depending upon the degree to which the outlet is opened or closed. For example, the sealing means may be operated to slide across the vent, such that the rate of flow of the liquid sample is slowed as the outlet is in a partially closed position. In an embodiment, the sealing means may adopt any one or more positions which partially close an outlet to alter the rate of flow in a passage. These embodiments may apply to both the first and second sealing means of the invention.

Conveniently, one or more outlets may be grouped together. Preferably where there is a side passage associated with a main passage, the pair of outlets for the main passage and side passage may be located within a close proximity so the respective sealing means are operable by a single control element. In an embodiment, two or more side passage outlets may be grouped in close proximity, and two or more main capillary passage outlets may be grouped in close proximity, so that each group may be controllable by a single control element. Preferably, outlets or groups of outlets may be located in close proximity to the fluid application region.

Preferably, the control element conveniently surrounds the fluid application region. A control element may be any suitable shape or size, preferably easily manipulated by the user. A control element may be manually operable by a user, or automatically operable, for example prompted by one or more sensors associated with detection means in the device, or a timer.

Sealing means or sealing components may carried on or forming part of the control element, e.g. on the underside thereof. The sealing means or components may be constituted by elements, e.g. of soft material, e.g. a soft thermoplastic material such as an elastomer, standing proud of or forming part of the control element underside. Sealing means or a sealing component may be provided on a flange which extends outward from a side wall of a control element, preferably substantially perpendicular thereto. Sealing means may be feet, provided on a flange.

Markings and/or stops are conveniently provided to indicate the various positions of the control element, to facilitate operation by a user. These may be provided preferably in the capillary pathway device.

End stops are desirably provided to limit the movement of the control element. Desirably, a control element is movable between a first, inactive position in which the liquid inlet is not in fluid communication with the fluid application region and the first sealing means do not seal the outlet(s) of the capillary passage(s) and a second position in which the liquid inlet is in fluid communication with the fluid application and the first sealing means seal the outlet of the first capillary passage. If side passages are present, second sealing means are positioned not to seal the outlet(s) of any side passages in the first, inactive position; and not to seal the outlet(s) of any side passages in the second position.

In embodiments having a side passage, the control element is moveable to a third position in which the first sealing means do not seal the outlet(s) of the first capillary passage(s), and the second sealing means seal the outlet(s) of a side passage (s). Preferably, in the third position, the liquid inlet is not in fluid communication with the fluid application region.

The control element may be of any suitable shape, preferably which allows it to move along or around or over the fluid application region. For example, it may be a rotatable element, for rotational movement about a pivot, or a formed for linear movement, e.g. a sliding motion along the location of outlets. Preferably, it is conveniently positioned for rotation in relation to fluid application region, e.g. in relation to a sample well (i.e. around, with or over) as discussed above. Where the sample well is defined by a generally cylindrical side wall carried by the control element, the side wall will rotate with the control element. Where the sample well is a recess or indent in the capillary pathway device and a control element forms a cover thereof, an underside of the control element may form the cover of the sample well. The sample well is exposed or covered depending on the position of the control element. Other suitable shapes and forms of the control element and fluid application region are included within the scope of the invention. Grooves and elements may be provided on the control element and upper surface of the device to permit limited movement of the control element relative to the well.

The control element may comprise a sample well, or serve as a cap for a sample well. It may include a liquid inlet for passage of liquid to the fluid application region, and thus the sample application hole. Preferably, the liquid inlet is in fluid communication with the fluid application region or sample well only when a control element is in selected positions, e.g. selected rotary or linear positions, as further described below.

In an alternative embodiment, the sample well is constituted by an element which is distinct from a control element of the device. In an embodiment, the fluid application region or sample well has a cap which is constituted by an element which is distinct from a control element of the device.

In an embodiment, the well side wall desirably includes a main cylindrical portion e.g. a part-cylindrical portion such as a part circular cylindrical portion, with a wider extension portion, e.g. a part-cylindrical portion such as a part circular cylindrical portion, with the extension portion base including an opening leading to the inlet of the capillary passage(s). The control element, e.g. rotatable cap, desirably includes a cooperating annular groove on the underside, dimensioned to fit around the well side wall, with the annular groove having a widened portion to accommodate the well side wall extension portion, with the control element having a fluid entry opening overlying the widened portion of the groove. The arcuate length of the widened portion of the control element groove is larger than the arcuate length of the well side wall extension portion, to permit limited rotary movement of the control element relative to the well.

In embodiments of the invention, for example where capillary action is used to move liquid sample in the passages, fluid dispensing means may be provided. Preferably, fluid dispensing means comprise a rupturable, sealed container of fluid to be dispensed, rupturing means for rupturing the container and releasing the contents, the container and rupturing means being arranged for relative movement between a first position in which the container is intact and a second position in which the container is ruptured.

Preferably, the fluid is a buffer, which serves to assist movement of the liquid sample in the passages, although the fluid may be any fluid required for performance of the assay. Where it is used to assist movement in a capillary based assay, the buffer may be referred to as a chase buffer. Any suitable buffer may be used, for example, a solution of Ficoll polymer, preferably a 1% by weight solution of Ficoll polymer in deionised or distilled water (Ficoll is a Trade Mark), which enables the reaction to be carried out with a smaller volume of sample than is required to flow around the entire capillary system to determine a test result.

The rupturable, sealed container of fluid may be movable with respect to rupturing means, e.g. in the form of projections in the vicinity of the fluid application region, for release of fluid for passage to the capillary pathway device. Operating means serve to move the container, rupturing means or both into a second position in which the container is ruptured. The operating means may be a plunger, carrying at one end either the container or rupturing means. Operating means may be arranged for rotary movement e.g. about a pivot, or linear movement (axially or laterally).

Preferably, at least a portion of the container wall is rupturable, e.g. being formed of rupturable foil such as a polyolefin film. The container may be made entirely of rupturable material e.g. being in the form of a capsule. As a further possibility, the container may mainly or partly comprise rigid material, e.g. a rigid plastics material, with a rupturable portion, such as a rupturable wall or base, e.g. of rupturable foil such as polyolefin film.

Any suitable rupturing means may be provided. Preferably, the rupturing means conveniently comprise one or more projections, preferably having sharp tips. The projections are desirably tapered, and preferably have features to facilitate fluid release e.g. being of scalloped configuration. Desirably a plurality of projections are provided.

Second rupturing means may similarly be provided, arranged to rupture an opposing portion of the container, to allow air to pass into the container. This aids flow of fluid out of the container. The second rupturing means may be provided as for the first rupturing means, provided they are arranged to rupture an opposing portion of the container.

Preferably, the rupturable container, at least when in a ruptured position, is in fluid communication with the fluid application region or sample well. Preferably, fluid communication means are provided to pass fluid from the container to the sample well or fluid application region. The fluid enters the capillary passage via the sample inlet hole, as defined above.

The fluid dispensing device may be a separate element, distinct from the capillary pathway device and fluid flow control device. If separate, it is preferably arranged to cooperate (be compatible with) with the capillary pathway device and/or the fluid flow control device. The fluid dispensing device may be provided on the capillary pathway device.

Alternatively, the fluid dispensing device may be provided by the fluid flow control device. Preferably, it is provided by the control element carrying the sealing means or a sealing component, as defined herein. Preferably, the rupturing means are provided on an inner surface of the base of the fluid flow control device. In such an embodiment, the rupturable container may be provided by the fluid flow control device (preferably the control element).

Alternatively, the fluid dispensing device may be composed of parts of the capillary pathway device and the fluid flow control device. For example, rupturing means may be provided by the capillary pathway device (for example, as moulded upstanding projections), and the rupturable container and operating means may be provided by the fluid flow control device.

In an embodiment, a single control element may be provided comprising sealing means (e.g. constituted by a sealing component), carrying means for a rupturable, sealed container of fluid (and optionally the container of fluid) and/or rupturing means and optionally operating means for bringing into contact a rupturable, sealed contained and rupturing means. Such a control element preferably also defines a portion of a sample well or fluid application region, for example as defined above.

In such an embodiment, movement of the control element to operate the sealing means may be combined with movement to rupture the container. Thus, for example, movement of the control element to operate the sealing means may also cause the container to be brought into contact with rupturing means. For example, in a preferred embodiment, rotational movement of the control element to operate the sealing means may also serve to drive operating means such that the container is brought into contact with rupturing means. In such an embodiment, a cam may be provided to operably link the rotational movement of the control element with a linear movement of the operating means.

Alternatively, movement of the control element to operate sealing means may be independent from the operating means to bring the container into contact with the rupturing means. Thus, separate actions are required.

Preferably, the control element is a control element comprising sealing means, as described herein.

The container is preferably movable relative to the rupturing means, although other arrangements are possible, such as the rupturing means being movable relative to the container, or both being movable to come into contact.

In one preferred arrangement, the container is arranged for downwards movement, to be brought into contact with rupturing means. In this embodiment, the rupturing means are preferably provided on the device, and preferably are in fluid communication with a sample well or fluid application region. The rupturing means may comprise projections, and the container is impaled onto upstanding projections. In another preferred embodiment, the container is arranged for impaling on projections and being pierced by spikes.

Preferably, the container or rupturing means are movable within the control element between the first and second positions, e.g. either being carried by or constituting a plunger operable from the exterior of the control element by simple application of force, e.g. manually by a user or in automated manner. The relative movement with respect to one another may be linear or axial. I.e. the operating means may effect a linear or axial movement. Activation brings the rupturing means and container into contact, thus releasing fluid from the container. Preferably, the same action brings second rupturing means into contact with the container, to allow air to pass into the container. Thus, preferably, fluid passes passively from the container.

In a preferred embodiment, the operating means comprise a plunger. The plunger may be initially retained in the first position, spaced from the rupturing means, e.g. by rupturable webs. On removal of the spacing means, for example, rupturing of the webs, the plunger is freed and can be moved to the second position in which the container is brought into contact with the rupturing means, and the contents are released. Preferably, the container is carried by the plunger. Preferably, the plunger is carried, or is part of, a control element. Preferably, the rupturing means are carried by the device, or a control element, or a distinct element. Instead of rupturable webs, a removable collar may be provided to prevent premature operation of the plunger. In a preferred embodiment, the removable collar includes a cap to cover the sample application region.

The fluid flow control device is conveniently used to dispense fluid to a fluid receptacle, e.g. for reaction therein, or to the inlet of a fluid flow passage.

This embodiment of the device of the invention is conveniently used in such sample test devices for supplying a known volume of reagent, e.g. a chase buffer, to the system. This enables the assay to be carried out using a smaller quantity of sample than would otherwise be required.

The invention can enable fluid to be dispensed reliably in known quantities, determined by the container contents, even small volumes such as 1000 microliters or less, 500 microliters or even less.

A device of the invention can thus be easy to operate, to deliver a predetermined volume of fluid, and can be used reliably by relatively unskilled personnel.

A control element as discussed above can be easily manipulated by a user, and can be used reliably by relatively unskilled personnel to deliver accurately controlled quantities of liquids.

Optionally, a timer is associated with a device of the invention. The timer may be used to indicate the time for moving the sealing means or a control element between positions, and/or for rupturing the container.

Preferably, one or more detection regions are provided in a capillary or side passage, to determine presence or absence of liquid sample at a detection region. Detection regions may be provided in a side passage, as described herein, and preferably one or more detection regions in a first capillary passage. Presence or absence of liquid sample at a detection region may prompt the user to move the sealing means (e.g. operate the control element) or otherwise control the flow of liquid sample, or rupture the sealed container.

Preferably, a capillary passage of the device, and optionally a side passage, may be treated to improve flow of liquid sample therethrough, by passing treatment fluid through the passage to leave a surface coating on the internal surface of the passage. Thus, a capillary passage of the device and optionally a side passage comprise a coating on the inner surface thereof, of a treatment fluid.

The coating typically acts by minimising any repulsion between the inner surface of the passage and sample fluid, whilst preferably not actively binding or substantially reacting with any sample, fluid or component thereof. Preferably, the surface coating increases the hydrophilicity of the passage, as compared to an untreated passage. The coating may, for example, act by forming a layer on the inner surface of the treated passage, polymerising with the surface of the treated passage, or soaking into the material of the treated passage.

The treatment fluid may be a liquid or a gas, but typically is a liquid. Preferably, the treatment fluid, when passing through the passage, coats the inner surface of the passage (as discussed above, by leaving behind a layer of material, soaking into the passage material or polymerising therewith, for example). This coating has the effect of altering the surface properties of the passage, for example to improve fluid (e.g. sample) flow though the passage, for example by improving the hydrophilicity of the passage. Preferably, the treatment fluid is one which improves flow of liquid sample, and does not bind to the sample.

Alternatively, the treatment fluid may be a reagent, for deposition in a passage. The treatment fluid may be a reagent, preferably an assay reagent, including for example reagents comprising agglutination reagents, antibodies, and labels. Other reagents include buffers, and any other assay components.

The thickness of the coating will depend upon the type of treatment fluid, the purpose of the coating, and the dimensions of the capillary passage. Where a layer of treatment fluid is left on the inner surface of the passage, it is preferably multi-molecular or mono-molecular layer. Preferably, the method of the invention causes substantially the entire inner surface of the treated passage to be coated with treatment fluid. Preferably, the inner surface comprises an open-topped channel formed within a component, and the cover member thereof. Where it is desired to improve flow through a passage, this can be achieved by use of a treatment fluid with suitable hydrophilic properties, e.g. a surfactants. Suitable materials are well known to those skilled in the art, and include for example polysorbates, commonly being used for this purpose, particularly polyoxyethylene sorbitan materials known as Tween (Tween is a Trade Mark), e.g. Tween 20 (polyoxyethylene (20) sorbitan monolaurate), Tween 60 (polyoxyethylene (20) sorbitan monostearate), Tween 80 (polyoxyethylene (20) sorbitan monooleate). Such materials are typically used in the form of dilute aqueous solutions, e.g 0.1 to 10%, typically. 1% by volume or less, typically in deionised water, although other solvents such as isopropanol (IPA) may alternatively be used.

The present invention provides a fluid flow control device, as described herein. The fluid control device may comprise a control element, as defined herein The present invention provides a capillary pathway device, as described herein.

The present invention provides a fluid dispensing device, as described herein.

DESCRIPTION OF THE DRAWINGS

A preferred embodiment of a sample testing device will now be described, by way of illustration, with reference to the accompanying drawings, in which.

DETAILED DESCRIPTION OF THE DRAWINGS

Figure 1:
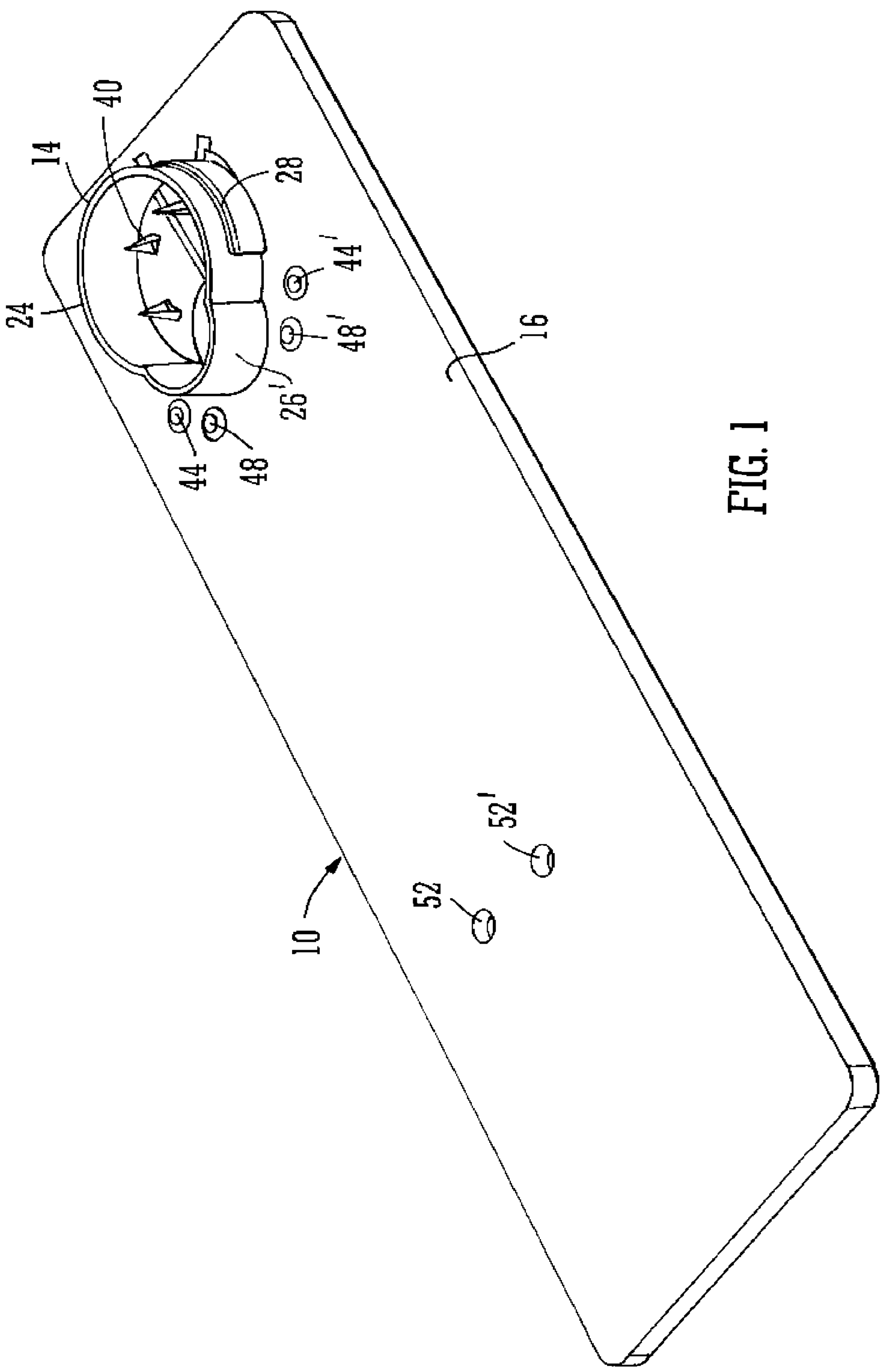
FIG. 1 is a perspective view from above of a sample collection element.

The drawings illustrate a sample testing device having capillary passages or pathways for performing an agglutination assay, e.g. generally as disclosed in WO 2004/083859 and WO 2006/046054.

The device comprises two main components: a sample collection element 10, and a cap 12. FIGS. 5 and 16 to 18 show a simplified version of the cap 12' for ease of understanding, with the plunger omitted for clarity. FIGS. 6 to 15 show a currently preferred version of cap 12. The caps 12 and 12' are functionally identical.

As shown in FIGS. 1 to 5, element 10 comprises a rigid, planar rectangular plate of injection moulded polycarbonate having dimensions 136 mm×57 mm×2.5 mm. The element is formed with an upstanding collar 14 on the upper face 16 thereof, with a series of grooves constituting open-topped channels 18 formed in the lower face 20 of the element. A series of holes, to be described below, extend through the element, opening onto the upper and lower faces.

Figure 3:
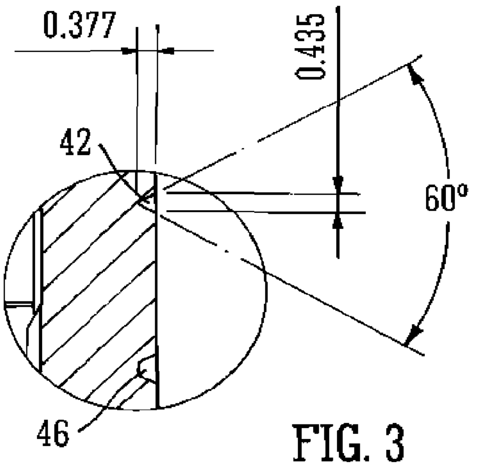
FIG. 3 shows to an enlarged scale part of the upper face of the device as shown in FIG. 1.
Figure 4:
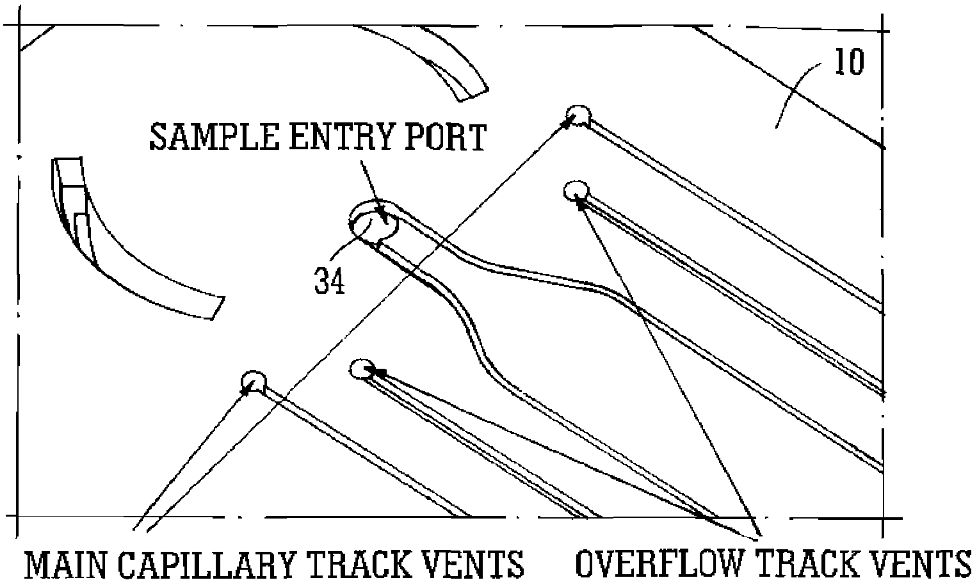
FIG. 4 shows to an enlarged scale part of the lower face of the device as shown in FIG. 2.
Figure 5:
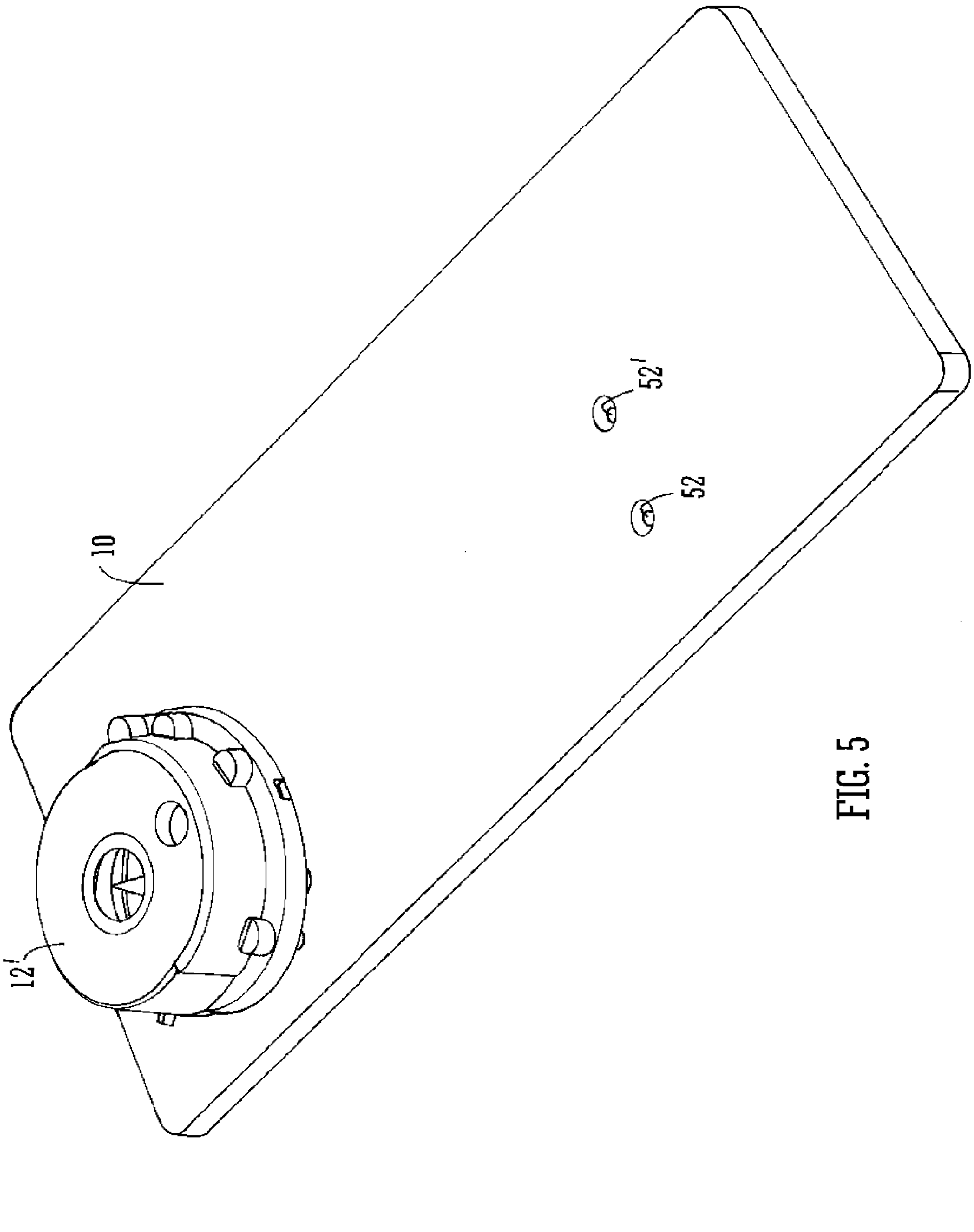
FIG. 5 is a perspective view from above of the element of FIGS. 1 to 4, carrying a simplified cap (with the plunger omitted for clarity)
Figure 6:
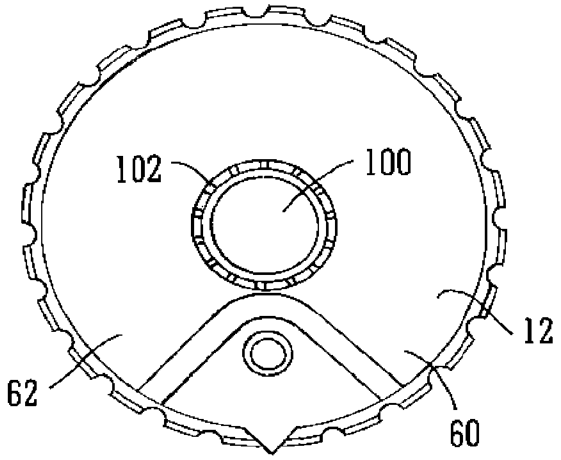
FIG. 6 is a top plan view of a preferred cap for use with the element of FIGS. 1 to 4.
Figure 7:
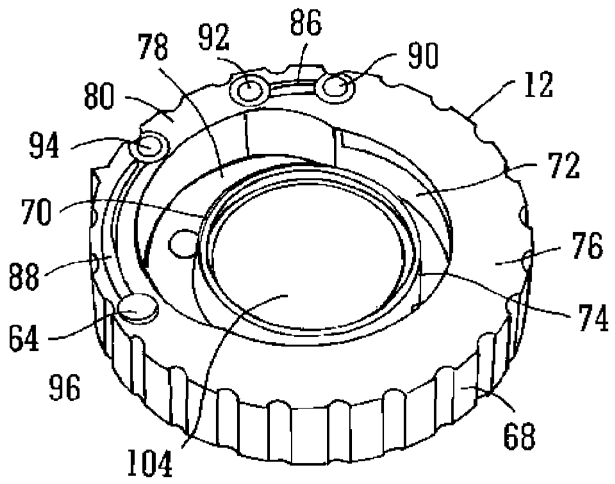
FIG. 7 is a perspective view of the underside of the cap shown in FIG. 6.
Figure 8:
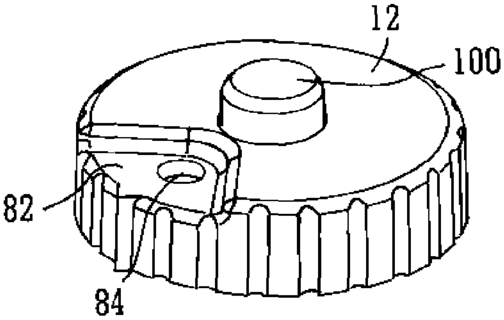
FIG. 8 is a perspective view from above of the cap of FIGS. 6 and 7, with the plunger in an upper, ready position.
Figure 9:
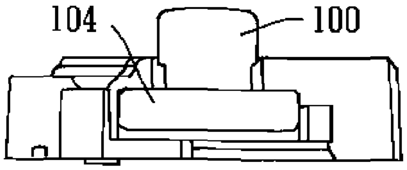
FIG. 9 is a sectional view of the cap of FIG. 8 with the plunger in the upper, ready position.
Figure 10:
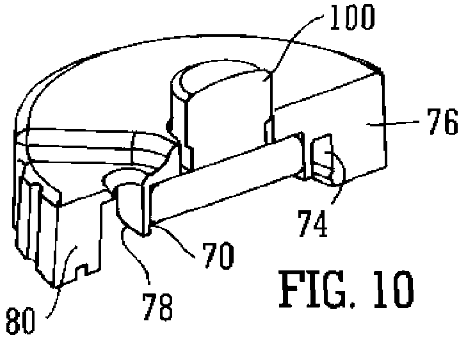
FIG. 10 is a cutaway perspective view of the cap of FIG. 8, with the plunger in the upper, ready position.
Figure 11:
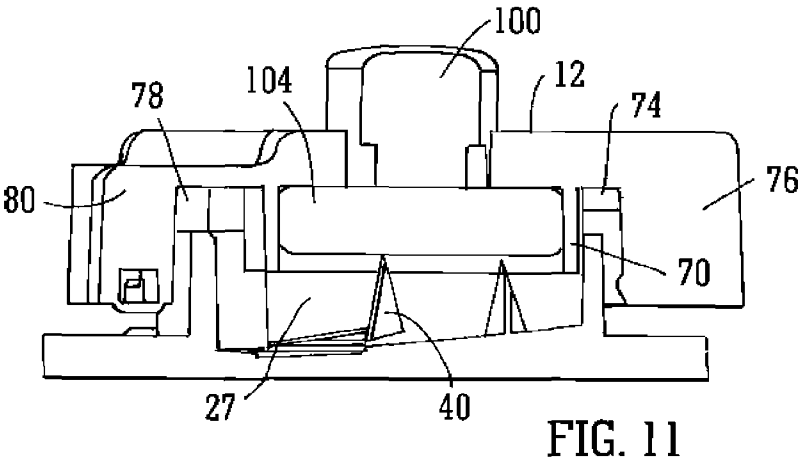
FIG. 11 is a sectional view, to an enlarged scale, showing the cap of FIGS. 6 to 10 located on the element of FIGS. 1 to 5, with the plunger in the upper, ready position.

As seen best in FIG. 3, the collar 14 is located near one corner of the element and includes a main part-circular portion 24 constituting part of a circle having a radius of about 10 mm and a minor part-circular portion 26 constituting part of a circle having a radius of about 6 mm. The collar 14 defines a generally cylindrical sample collection well 27 on the upper face of the element 10. A pair of ribs 28 extend outwardly over a portion of the outer surface of portion 24, with arcuate slot-shaped openings 30 extending through the element below the ribs. The openings do not perform any function in use of the device, and are present for moulding production reasons. The upper face of the element within the collar includes a circular funnel-like recessed portion 32 within collar minor portion 26, leading to a sample hole 34 extending through the element, with the remainder of the upper face of the element within the collar being slightly dished and downwardly inclined as shown at 36, as seen also in FIGS. 11 and 15. Four spikes 40 of scalloped configuration extend upwardly from the dished portion 36 of the upper face.

The channels 18 define two similar side-by-side capillary tracks, arranged as mirror images, constituting a test track and a control track. Each track comprises a main channel 42, 42' arranged in a U-shaped configuration, with major limbs about 100 mm long. These channels extend from the sample entry hole 34 to respective main channel vent holes 44, 44' that pass through the element 10. Each track also includes an overflow channel 46, 46' extending as a side branch from the associated main channel and turning through 90° to extend back towards the sample entry hole, and terminating in respective overflow channel vent holes 48, 48' extending through the element 10. The overflow channels are wider than the main channels. A short side channel 50, 50' extends from each of the main channels, slightly downstream of the junction with the overflow channels, terminating in respective side channel openings 52,52' extending through the element 10 and being countersunk on the element upper face.

Figure 2:
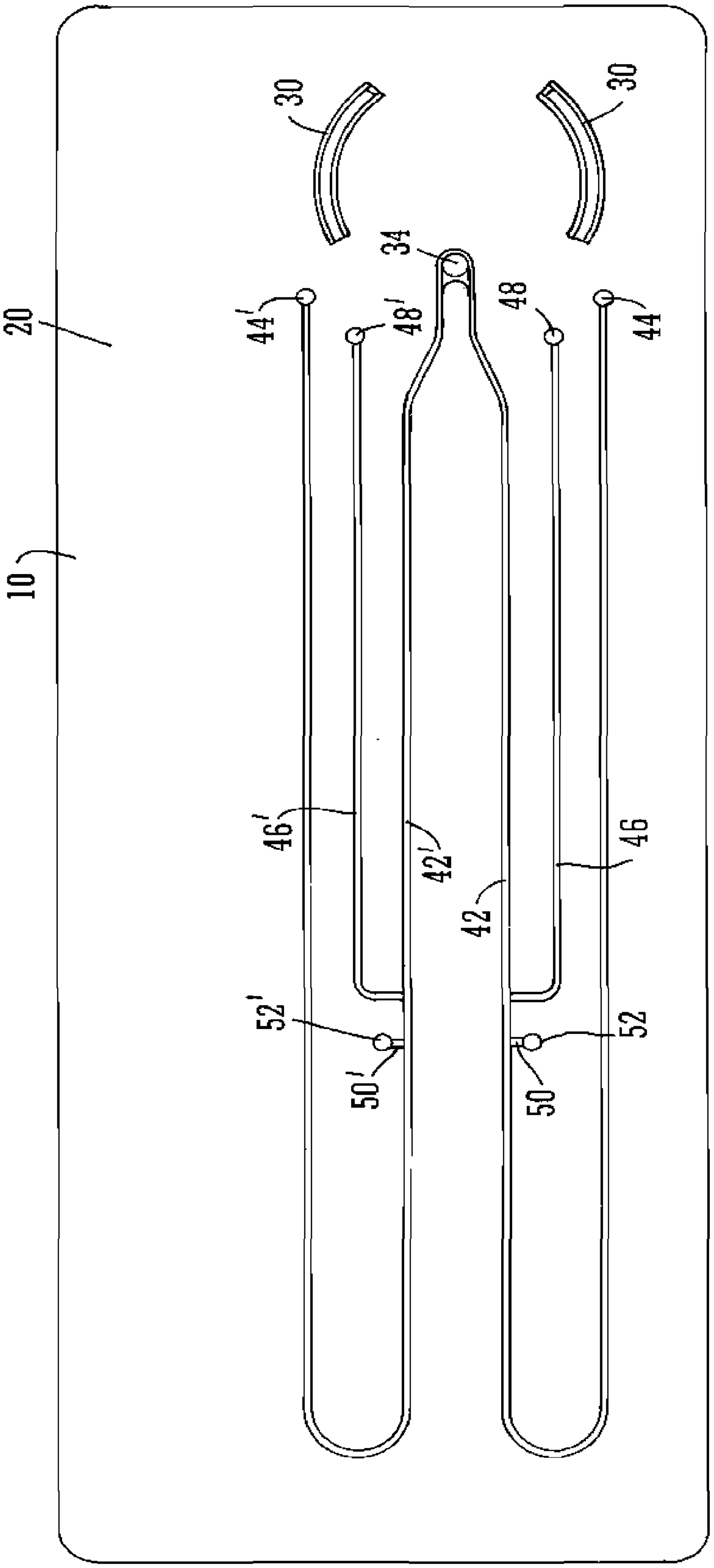
FIG. 2 is a plan view of the underside of the element of FIG. 1.
Figure 2A:
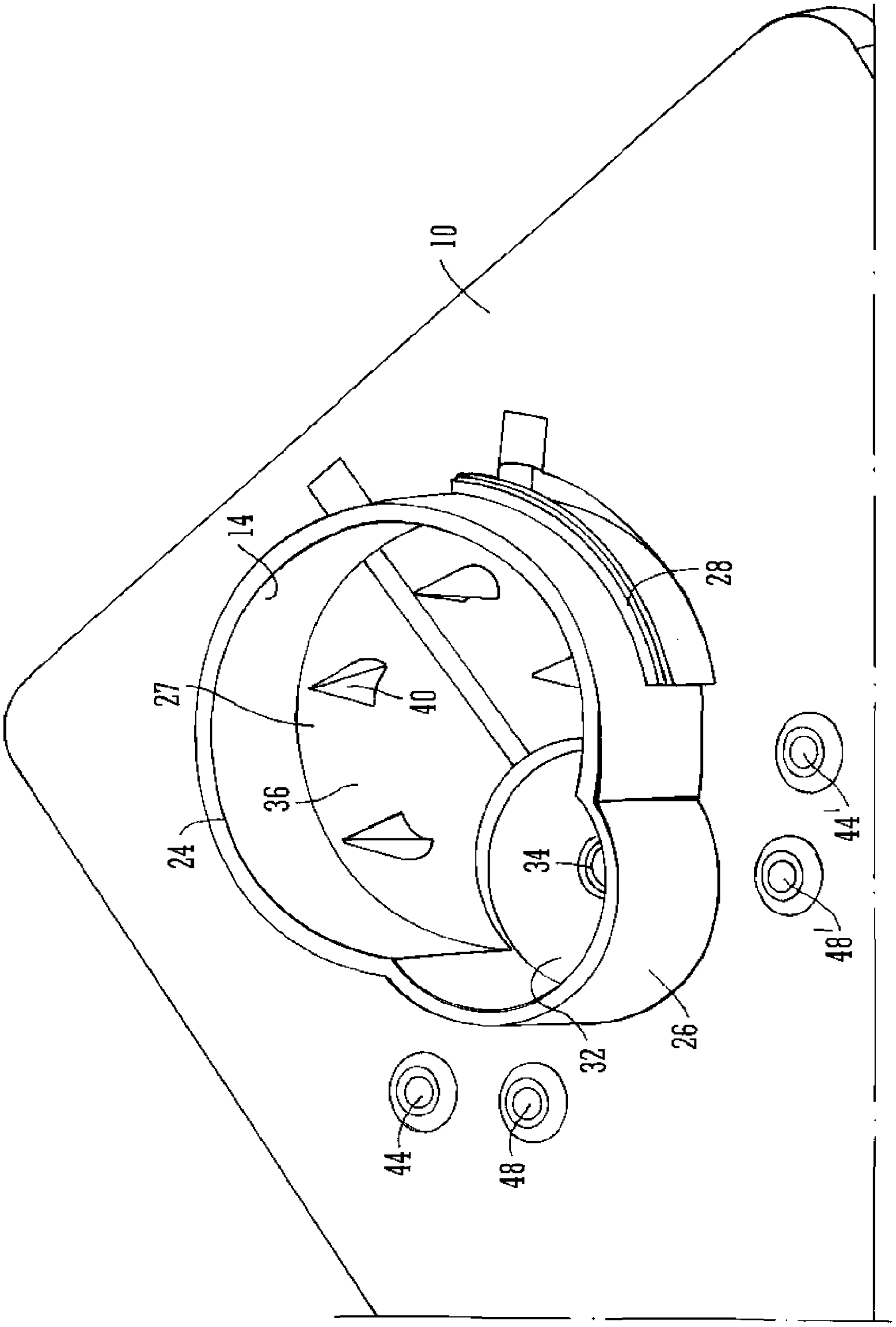
FIG. 2A is an enlarged scale sectional view of part of the element of FIGS. 1 and 2.

The main channels 42, 42' are V-shaped in section and have the cross-sectional profile of an equilateral triangle with sides 0.435 mm long. The depth of these channels is 0.377 mm. The overall length of each main channel is approximately 200 mm. The overflow channels 46, 46' are trapezoidal in cross section, having a flat base 0.3 mm in length with outwardly inclined side walls defining an angle of 60° therebetween. The depth of these channels is 0.38 mm. The overall length of each overflow channel is approximately 62 mm. The cross-sectional profile of the channels is shown in FIG. 2A.

The cap 12, 12' comprises a generally circular cylindrical, rigid body 60 of injection-moulded acrylonitrile butadiene styrene (ABS) with a diameter of about 34 mm and a height of about 10 mm. The body 60 has a circular upper wall 62 with a central opening 64, and a side wall 66 with a ribbed outer face 68. An inner cylindrical skirt 70 extends from the lower face of the upper wall 62, being centrally located with respect thereto, surrounding the central opening 64 and having a diameter greater than that of the opening 64. An annular trough 72 is formed between the inner face of side wall 66 and the outer face of skirt 70. A major, narrower portion 74 of the trough 72 has parallel side walls, defined in part by a part-circular thicker section 76 of side wall, with this portion 74 being configured and dimensioned to fit over the main portion 24 of the collar of element 10. The remaining minor, wider portion 78 of the trough 72 is defined in part by a thinner, curved section 80 of the side wall, with this portion 78 being sufficiently wide to fit over the minor portion 24 of the collar of element 10. The arcuate length of cap portion 78 is longer than the arcuate length of collar portion 26, so that when the cap 12 is located on the element 10 with the trough 72 located over the collar, a limited degree of rotary movement of about 90° of the cap 12 relative to the element 10 is possible, with the extent of movement determined by abutment of the ends of the inner face of thinner side wall section 80 with the outer face of the minor collar portion 26.

The upper wall 62 of the cap 12 includes a recessed portion 82 that has a sample entry hole 84 therethrough that is centrally and symmetrically located in the wider trough portion 78. Hole 84 cooperates with the sample entry hole 34 in the element 10, as will be described below.

The lower face of the cap thinner side wall section 80 includes two elongate part-circular grooves 86,88, each terminating in a circular recess. A cylindrical soft rubber insert 90, 92, 94, 96 of thermoplastic elastomer (TPE) with a Shore hardness of 40 A is fitted into each of the recesses, with the inserts standing slightly proud of the lower face of the side wall, forming four sealing members that cooperate with the capillary channel vent holes 44, 44', 48, 48', as will be described below.

Figure 12:
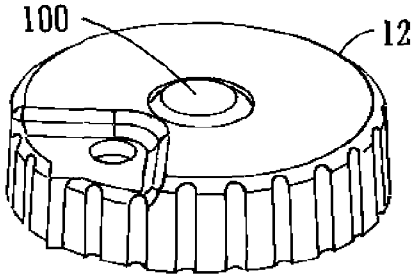
FIGS. 12 to 15 are a series of views corresponding to FIGS. 8 to 11, showing the plunger in a lower, depressed, activated condition position.
Figure 13:
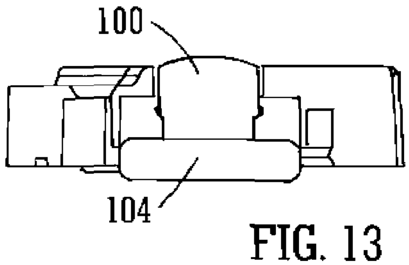
Figure 14:
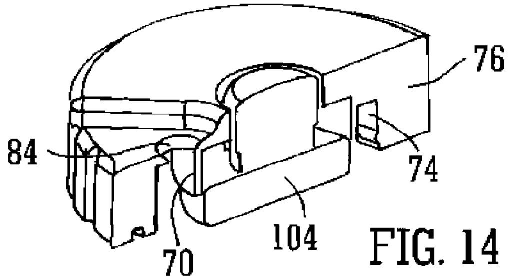

The cap 12 includes a generally cylindrical rigid plunger 100 of ABS located in the central opening 64 of the cap body 60 and connected to the body by a series of thin, rupturable webs 102. A fluid filled cylindrical polypropylene capsule 104 with a capacity of 400 microliters is carried on the lower end of the plunger 100, with the capsule being dimensioned to fit snugly within the skirt 70, for axial sliding movement therewithin. The plunger 100 and capsule 104 are movable between an upper, ready position, as shown in FIGS. 8 to 11, and a lower, activated position, as shown in FIGS. 12 to 14, by application of a suitable downwards force to the plunger to rupture the webs 102 and cause axial movement of the plunger 100 and capsule 104 relative to the cap body 60 and element 10, causing the capsule 104 to be impaled on the spikes 40 with consequential release of the fluid contents into the well 27 formed within collar 14.

A sheet of flexible foil 106 (FIG. 15A) in the form of a clear polycarbonate sheet 0.06 mm thick is secured by laser welding to the lower face 20 of the element 10 to cover the channels 42, 42', 46, 46' and side channels 50, 50' and convert them into enclosed capillary passages, also referred to herein as capillary pathways.

Hydrocarbonates such as polycarbonate or ABS are hydrophobic which means that aqueous fluids will not flow well within the passages. To address this, the capillary passage internal surfaces are treated to provide a thin coating of Tween 20 surfactant (Tween is a Trade Mark) to impart hydrophilic properties to the capillary surface. This can be done by any suitable means, for example by using a vacuum process to draw a solution of Tween 20 in deionised water (comprising 0.25% by volume Tween 20) through the capillary passages, by applying suction at an open end of the passages. This is illustrated schematically in FIG. 15A. The Tween 20 solution is applied via the sample entry hole 34, and a pair of suction cups are applied to the vent holes at the ends of the capillary passages, first to the main passages and then to the overflow passages. A vacuum is applied by means of a vacuum generator, and acts to suck the Tween 20 solution through the passages as represented by the arrows in FIG. 15A. The element 10 is then left to dry in an oven at low temperature to evaporate the water part of the solution, leaving behind the Tween 20 deposited as a thin layer on the internal capillary surfaces, thus making the surfaces hydrophilic.

This treatment also performs a quality control function in that it will reveal if any of the capillary passages are blocked, e.g. as a result of imperfect moulding, imperfect sealing of the foil, or the presence of debris or foreign matter in the passages, enabling defective elements to be discarded at this stage.

The device is prepared for use in agglutination assay by depositing a controlled amount of agglutination reagent, e.g. as disclosed in WO 2004/083859 and WO 2006/046054, in the test track passage 42. Any suitable method can be used to deposit the reagent. A preferred method is via side channel 50, with reagent being added via opening 52. A liquid comprising the reagent is supplied via opening 52, and a vacuum applied to the vent hole 44. This acts to suck the liquid through the side channel 50 and the downstream part of test track passage 42, in the same manner as the Tween treatment described above, resulting in deposition of reagent on the capillary wall along the downstream part of the passage 42. This is followed by drying as required. The openings 52, 52' are then sealed by application of a foil covering to produce an air-tight seal.

Figure 16A:
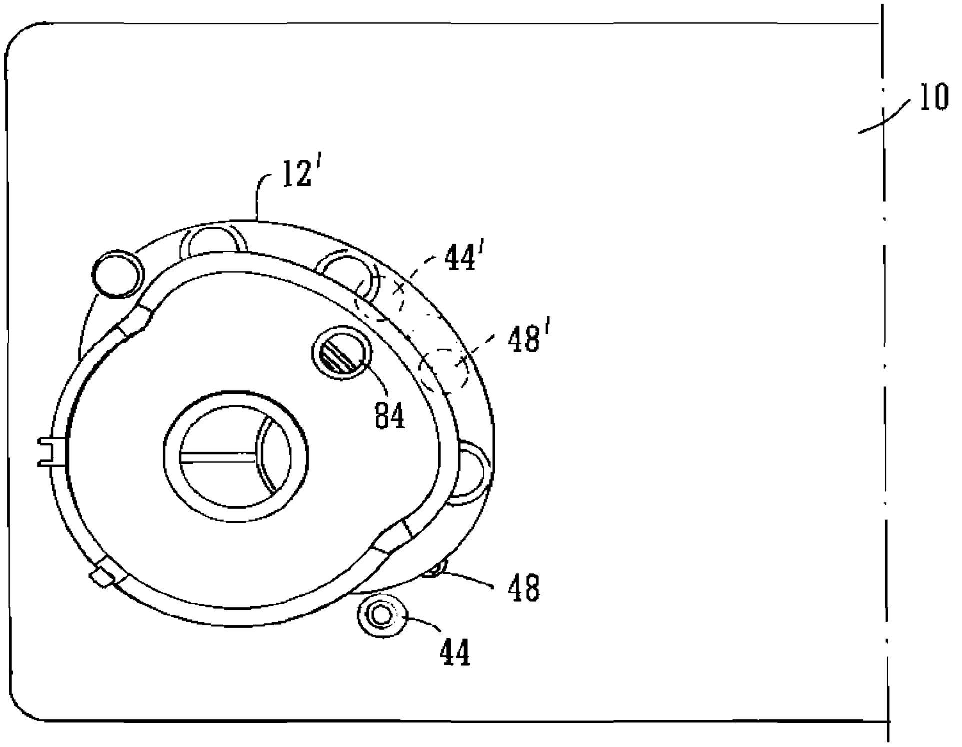
FIGS. 16A and 16B are top plan and underside plan views, respectively, of part of the element of FIGS. 1 to 5 with the simplified cap of FIG. 5 (with the plunger omitted for clarity), with the cap in a first position, with the top view also showing the position of parts in the element and the underside view also showing the underside of the cap.
Figure 16B:
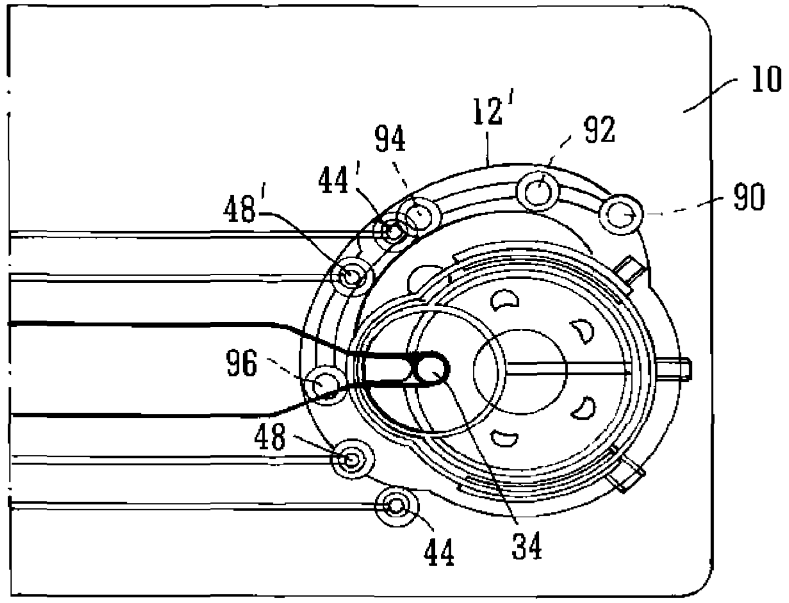

The cap 12 is then located on the collar 14 of the sample collection element 10, with the plunger 100 in the ready position and with the cap in a first position, as illustrated in FIGS. 16A and 16B. In this first position, the device is in an inactive state. The sample entry hole 84 of the cap is positioned so as not to be in fluid communication with the sample collection well 27 of the element, as shown in FIGS. 16A and 16B, so that the sample entry hole 34 of the element is effectively blocked. None of the channel vent holes is sealed.

The device in this condition may be packaged for distribution and sale, e.g. being sealed in a foil pouch which is impermeable to air and moisture.

Figure 17A:
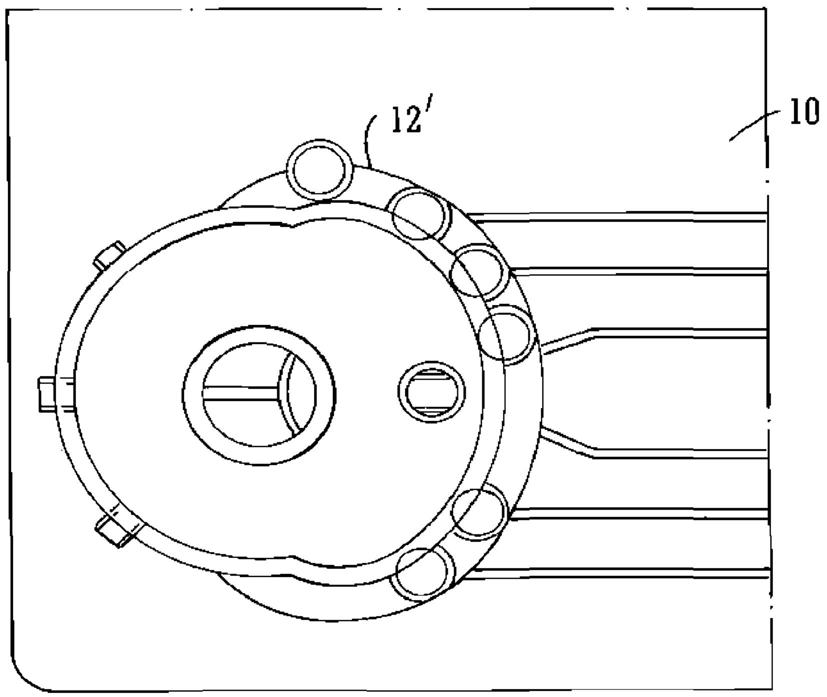
FIGS. 17A and 17B are views similar to FIGS. 16A and 16B, with the cap in a second position.
Figure 17B:
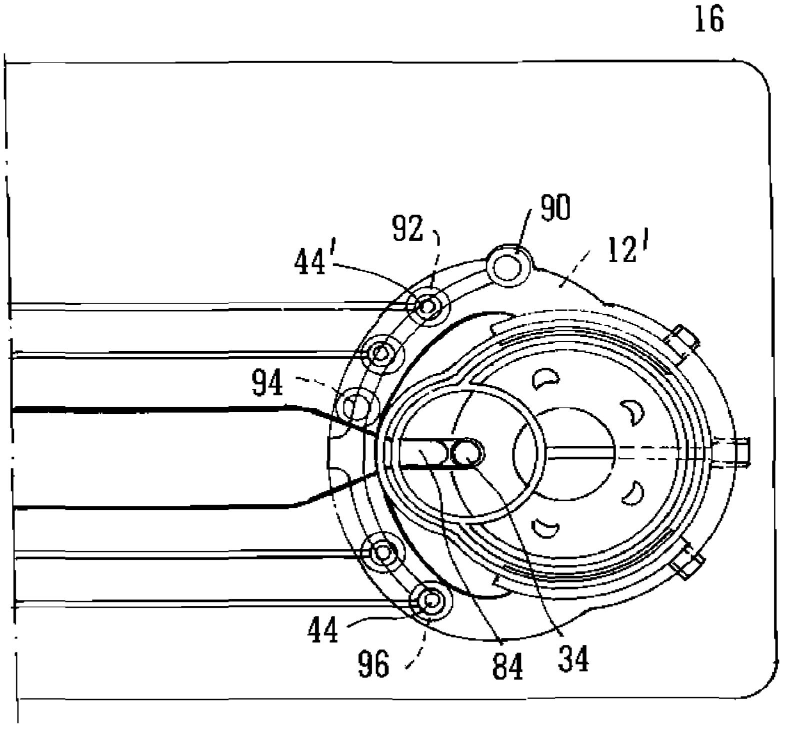

When the device is required for use, the cap 12 is rotated to a second position, as illustrated in FIGS. 17A and 17B. In this position the sample entry hole 84 of the cap is positioned over the portion 26 of the sample collection well 27, and is thus in fluid communication with the sample entry hole 34 of the element. In addition, the main channel vent holes 44, 44' are sealed by cap inserts 96, 92, respectively, while the overflow channel vent holes 48, 48' are not sealed.

Figure 19:
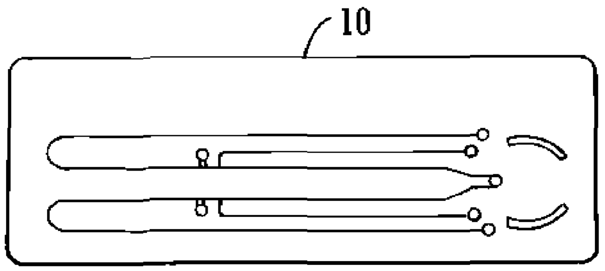
FIGS. 19 and 20 are schematic views of the underside of the element of FIGS. 1 to 5, representing operation with the cap in the second and third positions, respectively.

A quantity of fluid sample e.g. a blood sample to be tested (possibly containing an analyte of interest) is added to the device via sample entry hole 84. It is important that more sample is added than is required for the test, with a sample of about 15 microliters being appropriate in the present case. The sample fluid flows along the initial portions of the main passages 42, 42' and then into the overflow passages 46, 46', as illustrated in FIG. 19. In this figure, the sample is represented by filled regions. The sample cannot flow further along the main passages 42, 42' because the main channel vent holes 44, 44' are sealed by the cap. In this way, a defined quantity of sample is present in each of the main passages (referred to as the test volume), with excess being passing into the overflow passages. In the present embodiment, the test volume in each main passage is about 5 microliters.

Figure 18A:
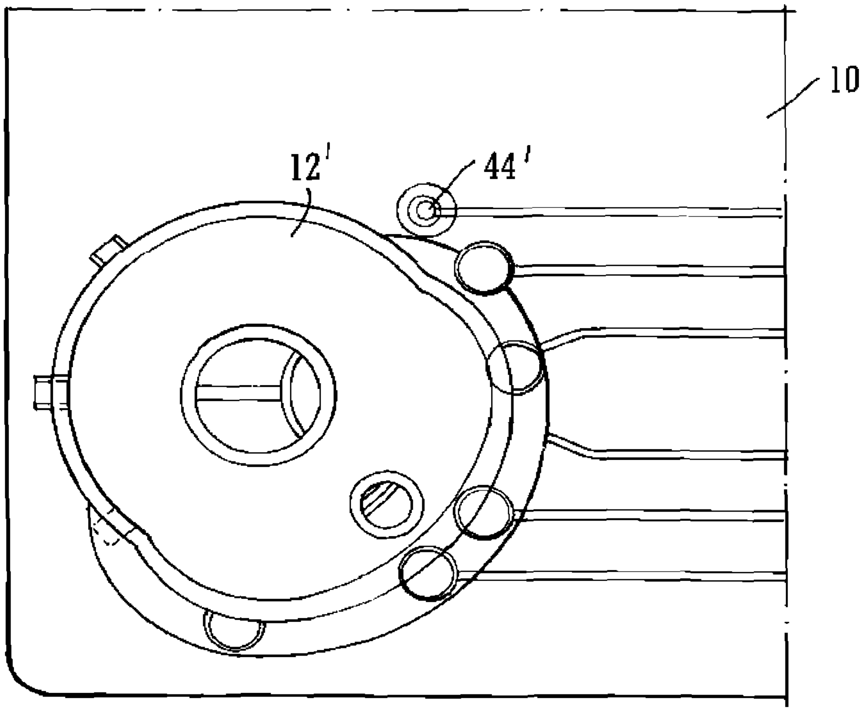
FIGS. 18A and 18B are views similar to FIGS. 16A and 16B, with the cap in a third position.
Figure 18B:
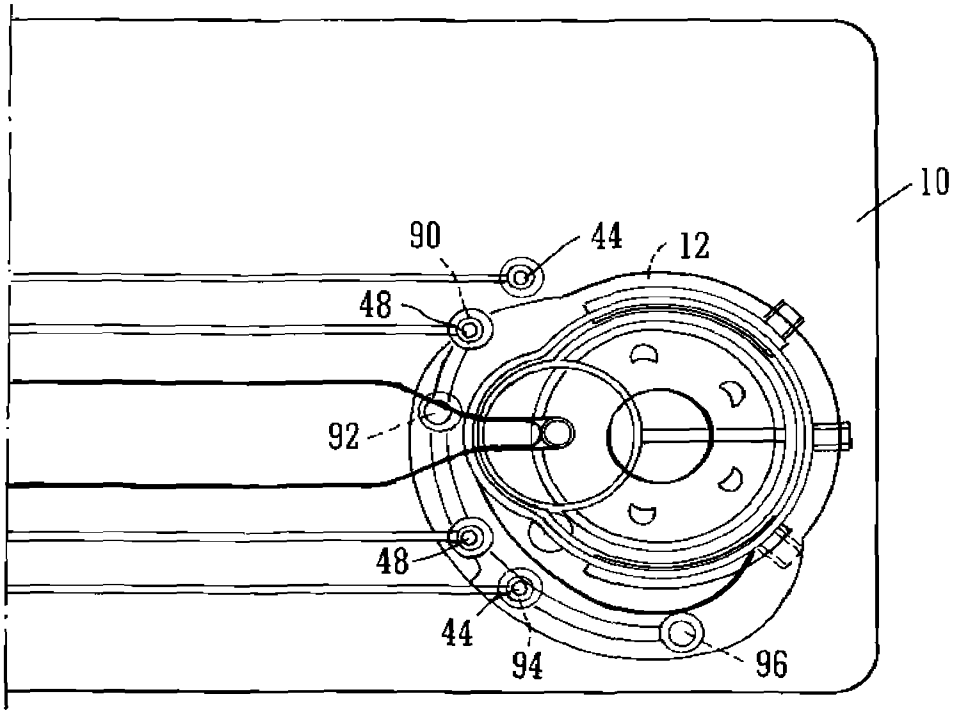

The cap 12 is then rotated to a third position, as illustrated in FIGS. 18A and 18B. In this position the sample entry hole 84 of the cap is again positioned so as not to be in fluid communication with the sample collection well 27 of the element, as in the first position. However, the overflow channel vent holes 48, 48' are now sealed by cap inserts 94, 90, respectively, while the main channel vent holes 44, 44' are not sealed.

Fluid in the capsule 104 is then introduced to the capillary passages. Preferably, this is after a predetermined time, e.g. as indicated by a timer associated with the device. Typically the fluid is a chase buffer, e.g. a 1% by weight solution of Ficoll polymer in deionised or distilled water (Ficoll is a Trade Mark), which enables the reaction to be carried out with a smaller volume of sample than is required to flow around the entire capillary system to determine a test result. This is achieved by operation of the cap plunger 100.

Figure 15:
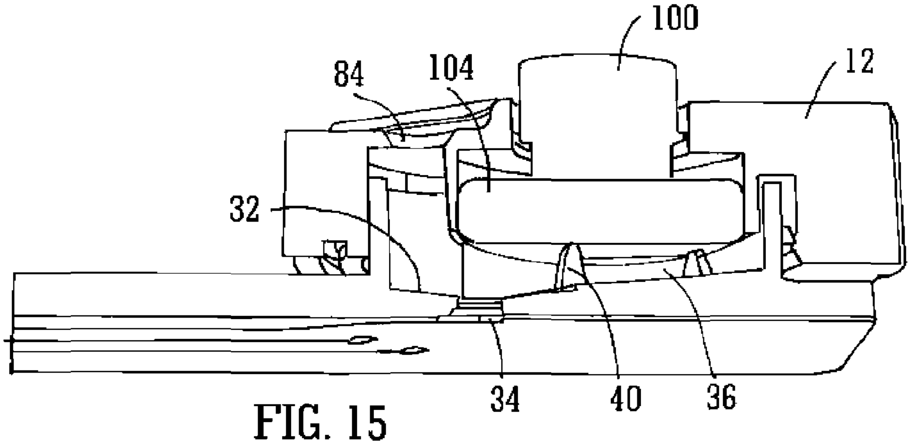
Figure 15A:
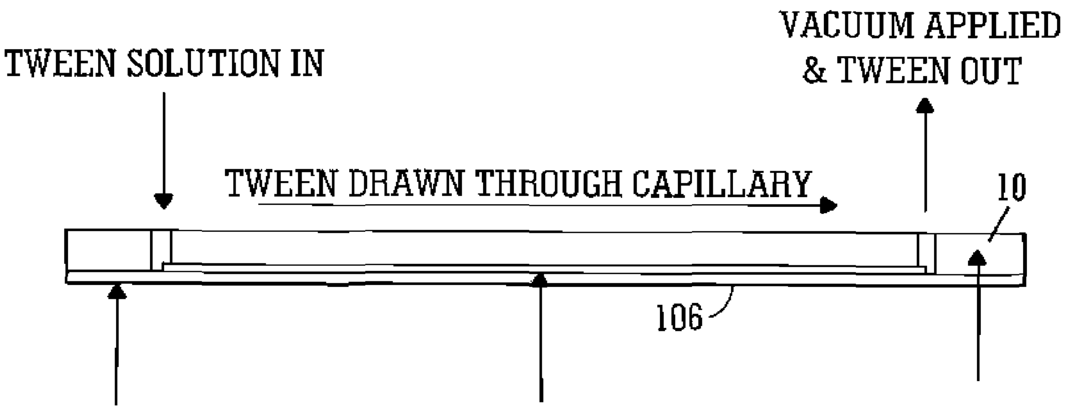
FIG. 15A is a schematic representation of a step in the production of the illustrated device.
Figure 20:
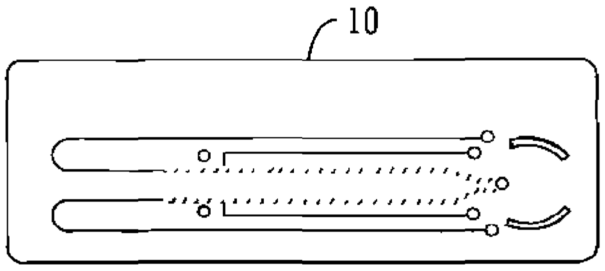

The plunger 100 of the cap 12 is depressed, e.g. by application of force by an operator, to move it to the activated position, as shown in FIGS. 12 to 15, resulting in piercing of the capsule 104 by the spikes 40, as shown in FIG. 15, and release of fluid from the capsule to flow into the well 27. As illustrated in FIG. 20, the capsule fluid, e.g. chase buffer, which is represented by hatched regions, pushes the test sample further along the main passages.

Sample (followed by chase buffer) will flow along the main passages 42, 42' by capillary flow. Because the overflow channel vent holes 48, 48' are now sealed, no further flow will take place along the overflow passages, including no backflow towards the main passages. Instead, fluid flow will be along the main passages 42, 42', towards the unsealed main channel vent holes 44, 44'. The sample will thus flow past the deposited reagent in the test passage. If the analyte of interest is present in the sample, this will react with the reagent, affecting the flow properties compared with unreacted sample in the control track.

The device includes a detector arrangement (not shown) near the ends of the main passages to detect the presence (or otherwise) of liquid in the test track and control track. From this, it can be determined whether reaction has taken place with the agglutination reagent, and information (qualitative or quantitative) can be determined about the presence of the analyte of interest in the test sample. Suitable detector arrangements are known, and are outside the scope of this invention.

The device is easy to use, and can be used reliably by relatively unskilled personnel, possibly at the point of care of patients. In particular, the device functions to provide a predetermined volume of sample into the capillary test system, by the operation of the overflow passages, and a predetermined volume of reagent such as chase buffer from the capsule. The device requires only a very small volume of sample to be tested, e.g. about 10 to 15 microliters. The device is intended for single use, being disposed of after use.

Figure 21:
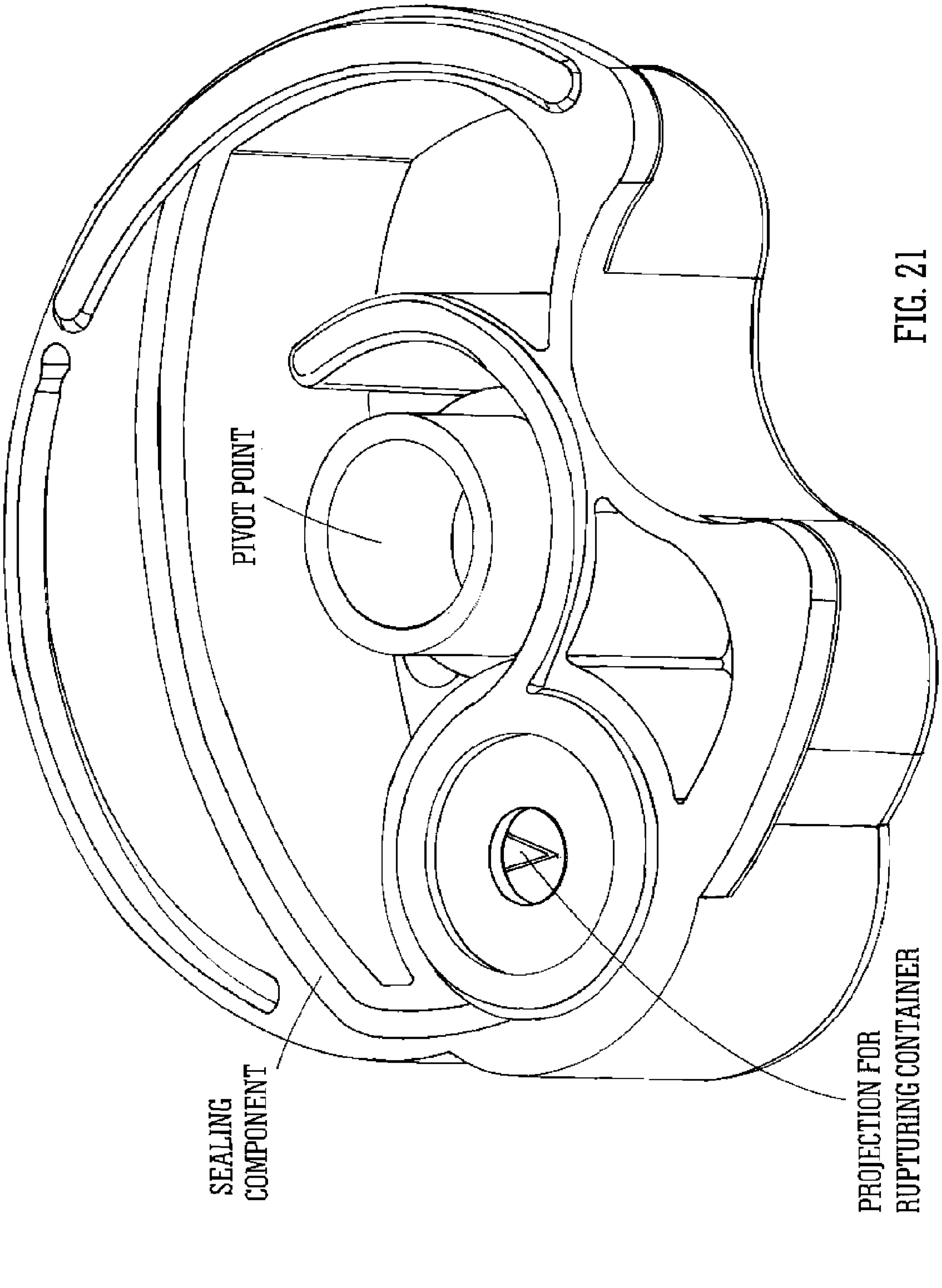
FIG. 21 is a view of the underside of a preferred combined control element of the invention, comprising sealing means, a plunger for a rupturable container, rupturing means, and serving as a cap for a sample well.
Figure 22:
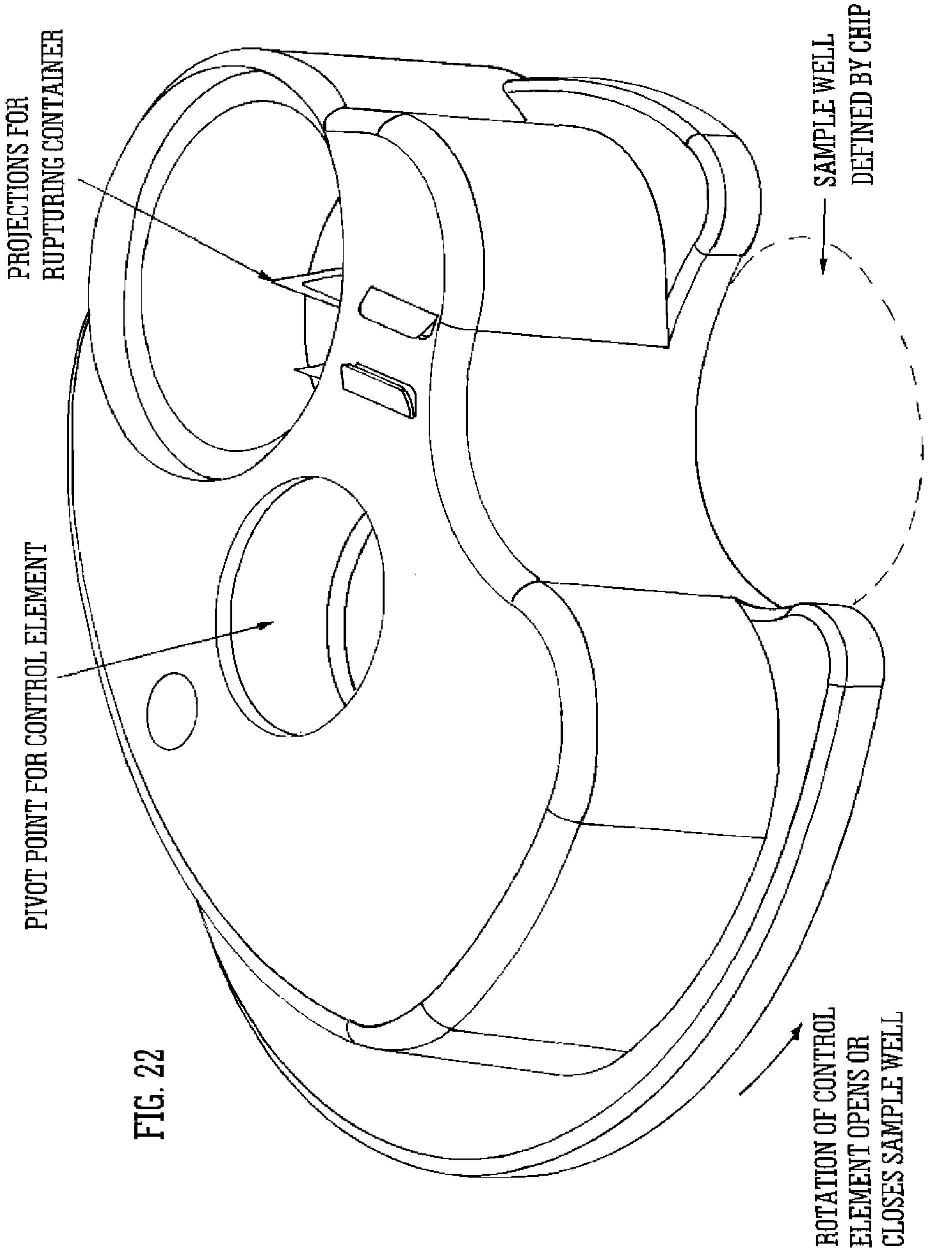
FIG. 22 is a top view of the same control element.

FIGS. 21 and 22 show an alternative embodiment of a control element according to the invention. In these embodiments, the control element is formed by a generally oval shaped member, comprising an underside portion on which sealing components are provided on the feet of the control element, such that the sealing components contact the upper surface of the planar capillary pathway device. A generally cylindrical well is formed within the upper surface of the control element, defined by side walls, and having a base portion with an hole which is in fluid communication with the sample entry hole of the capillary pathway device. The base of the well comprises sharp tapered projections. A pivot point is provided, enabling the control element to be rotated around the pivot point. The control element sits on the upper surface of the planar capillary pathway device, and is positioned such that in a first position (as shown) a sample well in the capillary pathway device is exposed. The sample well comprises a fluid application region, and in use, a user inserts the sample into the sample well. Operation of the control element enables it to be rotated about the pivot, so that an underside portion of the control element sits over the sample well.

We claim:

1. A device comprising:

i) a capillary pathway device comprising a first capillary passage with an inlet and an outlet and a fluid application region for receiving a liquid sample for entry to the capillary passage via the inlet ii) a fluid flow control device for controlling flow of fluid in a capillary pathway device, comprising first sealing means operable for releasably sealing the outlet of the first capillary passage, wherein the sealing means (and additional sealing means if present) are located on a control element which is movable to cause operation of the sealing means;

wherein the control element is mounted for motion with, around or over the fluid application region.

2. A device according to claim 1, wherein the control element is movable between a first, inactive position in which the liquid inlet is not in fluid communication with the fluid application region and the first sealing means do not seal the outlet(s) of the capillary passage(s) and a second position in which the liquid inlet is in fluid communication with the fluid application and the first sealing means seal the outlet of the first capillary passage.

3. A device according to claim 1, wherein the capillary pathway device comprises a side passage, and the fluid flow control device comprises second sealing means positioned not to seal the outlet(s) of any side passages in the first, inactive position; and not to seal the outlet(s) of any side passages in the second position.

4. A device according to claim 2, wherein the control element is movable to a third position in which the first sealing means do not seal the outlet(s) of the first capillary passage(s), and any second sealing means seal the outlet(s) of any side passage(s), and preferably, the liquid inlet is not in fluid communication with the fluid application region.

5. A device according to claim 1 wherein a sample well is provided as a recess or indent in the capillary pathway device and an underside of the control element forms a cover of the sample well, preferably such that rotation of the control element causes the cover to expose or conceal the sample well.

6. A device according to claim 1 wherein two or more sealing means are constituted by a single sealing component.

7. A device according to claim 6 wherein a sealing component is carried on or forming part of a control element.

8. A device according to claim 1 wherein two or more first sealing means are constituted by a single sealing component, moveable between a first position in which the first sealing means is positioned to seal the outlet of the first capillary passage and a second position in which the sealing means are positioned not to seal the outlet of a first capillary passage.

9. A device according to claim 6 wherein two or more second sealing means are constituted by a single sealing component moveable between a first position in which the second sealing means are positioned to not seal an outlet of a side passage and a second position in which the sealing means are positioned to seal an outlet of a side passage.

10. A device according to claim 6 wherein the component is movable between a first position in which the first sealing means is positioned to seal the outlet of the first capillary passage and the second sealing means is positioned not to seal the outlet of the side passage; and a second position in which the first sealing means is positioned not to seal the outlet of a capillary passage and the second sealing means is positioned to seal the outlet of the side passage.

11. A device according to claim 1 wherein two or more first sealing means and two or more second sealing means, or a sealing component, are/is provided on a control element, which is moveable between a first position in which the first sealing means is positioned to seal the outlet of the first capillary passage and the second sealing means is positioned to not seal the outlet of the side passage; and a second position in which the first sealing means are positioned not to seal the outlet of a first capillary passage and the second sealing means are positioned to seal the outlet of a side passage.

12. A device according to claim 1, comprising fluid dispensing means.

13. A device according to claim 12 wherein movement of the control element to operate the sealing means may be combined with movement to release fluid from the fluid dispensing means.

14. A device according to claim 13 wherein a cam is provided to operably link rotational movement of the control element with a linear movement of operating means of the fluid dispensing device.

15. A device according to claim 1 comprising a timer.

16. A device according to claim 1 wherein detection means are provided in a capillary passage, and optionally if present in a side passage, for determining presence of absence of sample liquid.

17. A device according to claim 16 wherein the detection means are operably linked to a control element of the device.

18. A device according to claim 1 wherein a capillary passage incorporates a reagent system capable of causing a reaction with a component of interest.

19. A device according to claim 1 wherein the device further comprises sample metering means.

* * * * *